United States Patent
Li et al.

(10) Patent No.: US 9,469,647 B2
(45) Date of Patent: Oct. 18, 2016

(54) SALT CRYSTALS

(71) Applicant: INTRA-CELLULAR THERAPIES, INC., New York, NY (US)

(72) Inventors: Peng Li, New York, NY (US); Lawrence P. Wennogle, New York, NY (US); Robert Davis, New York, NY (US); Graham Buckton, Fleet (GB); Mark Hooper, Witney (GB)

(73) Assignee: INTRA-CELLULAR THERAPIES, INC., New York ( * ) Notice: Subject to any disclaimer, the term of this patent is extended or adjusted under 35 U.S.C. 154(b) by 0 days.

(21) Appl. No.: 14/409,988

(22) PCT Filed: Jun. 21, 2013

(86) PCT No.: PCT/US2013/047123
§ 371 (c)(1),
(2) Date: Dec. 19, 2014

(87) PCT Pub. No.: WO2013/192556
PCT Pub. Date: Dec. 27, 2013

(65) Prior Publication Data
US 2015/0259353 A1    Sep. 17, 2015

Related U.S. Application Data

(60) Provisional application No. 61/662,355, filed on Jun. 21, 2012.

(51) Int. Cl.
| C07D 487/14 | (2006.01) |
| A61K 31/519 | (2006.01) |
| A61P 35/00 | (2006.01) |
| C07C 55/02 | (2006.01) |
| C07C 57/15 | (2006.01) |
| C07C 309/04 | (2006.01) |

(52) U.S. Cl.
CPC ............. C07D 487/14 (2013.01); C07C 55/02 (2013.01); C07C 57/15 (2013.01); C07C 309/04 (2013.01); *C07B 2200/13* (2013.01)

(58) Field of Classification Search
CPC . C07D 487/04; C07D 401/10; A61K 31/519
USPC .................................. 544/247; 514/257, 247
See application file for complete search history.

(56) References Cited

U.S. PATENT DOCUMENTS

| 8,273,750 B2 | 9/2012 | Li et al. |
| 8,273,751 B2 | 9/2012 | Li |
| 8,536,159 B2 | 9/2013 | Li et al. |
| 8,633,180 B2 | 1/2014 | Li et al. |
| 8,664,207 B2 | 3/2014 | Li et al. |
| 8,829,008 B2 | 9/2014 | Li |
| 8,858,911 B2 | 10/2014 | Li et al. |
| 9,000,001 B2 | 4/2015 | Li et al. |
| 9,006,258 B2 | 4/2015 | Fienberg et al. |
| 9,198,924 B2 | 12/2015 | Mates et al. |
| 2001/0034450 A1 | 10/2001 | Alexander et al. |
| 2004/0152712 A1 | 8/2004 | Bunnage et al. |
| 2005/0075795 A1 | 4/2005 | Pandit |
| 2005/0080107 A1 | 4/2005 | Ochiai et al. |
| 2008/0188492 A1 | 8/2008 | Li et al. |
| 2010/0087450 A1 | 4/2010 | Mates et al. |
| 2010/0273754 A1 | 10/2010 | Li et al. |
| 2010/0323997 A1 | 12/2010 | Fienberg |
| 2011/0237561 A1 | 9/2011 | Li et al. |
| 2011/0312978 A1 | 12/2011 | Davis |
| 2012/0053190 A1 | 3/2012 | Fienberg et al. |
| 2012/0070443 A1 | 3/2012 | Movsesian |
| 2012/0071450 A1 | 3/2012 | Li et al. |
| 2012/0238589 A1 | 9/2012 | Li et al. |
| 2013/0018063 A1 | 1/2013 | Li et al. |
| 2013/0085123 A1 | 4/2013 | Li et al. |
| 2013/0331363 A1 | 12/2013 | Li et al. |
| 2014/0005155 A1 | 1/2014 | Li et al. |
| 2014/0011783 A1 | 1/2014 | Li et al. |
| 2014/0148421 A1 | 5/2014 | Li et al. |
| 2014/0194396 A1 | 7/2014 | Li et al. |
| 2014/0357606 A1 | 12/2014 | Li et al. |
| 2015/0038474 A1 | 2/2015 | Li et al. |
| 2015/0072965 A1 | 3/2015 | Li et al. |
| 2015/0080357 A1 | 3/2015 | Li et al. |
| 2015/0139903 A1 | 5/2015 | Li et al. |
| 2015/0197528 A1 | 7/2015 | Li et al. |
| 2016/0083390 A1 | 3/2016 | Li et al. |

FOREIGN PATENT DOCUMENTS

| WO | WO 2006/133261 A2 | 12/2006 |
| WO | WO 2008/063505 | 5/2008 |
| WO | WO 2008/070095 | 6/2008 |

(Continued)

OTHER PUBLICATIONS

International Search Report & Written Opinion of PCT/US2013/047123 issued on Dec. 6, 2013.
International Search Report of WO/2013/192556, mailed Dec. 6, 2013.
International Search Report of WO/2014/205354, mailed Apr. 3, 2015.
U.S. Appl. No. 14/492,879, filed Sep. 22, 2014, Peng Li, et.al.
U.S. Appl. No. 14/671,531, filed Mar. 27, 2015, Peng Li, et.al.
Bowker, "A Procedure for Salt Selection and Optimization". Handbook of Pharmaceutical Salts: Properties, Selection, and Use, Chapter 7, 2002, pp. 162-173.
Lee et al., "Large-Scale Aspects of Salt Formation: Processing of Intermediates and Final Products". Handbook of Pharmaceutical Salts: Properties, Selection, and Use, Chapters 8, 2002, pp. 191-192,211-214.
Stahl et al., "Monographs on Acids and Bases". Handbook of Pharmaceutical Salts: Properties, Selection, and Use, Chapters 12, 2002, 265-266, 282-283.

*Primary Examiner* — Venkataraman Balasubramanian
(74) *Attorney, Agent, or Firm* — Hoxie & Associates LLC

(57) ABSTRACT

The present invention relates to acid addition salt and salt crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4 (2H)-one, composition comprising the same and the method of making and using such salt and crystal.

31 Claims, 6 Drawing Sheets

(56) References Cited

FOREIGN PATENT DOCUMENTS

| WO | WO 2009075784 A1 * | 6/2009 | ........... C07D 487/14 |
| WO | WO 2010/065148 | 6/2010 | |
| WO | WO 2010/065149 | 6/2010 | |
| WO | WO 2010/065151 | 6/2010 | |
| WO | WO 2010/098839 | 9/2010 | |
| WO | WO 2010/132127 | 11/2010 | |
| WO | WO 2011/043816 | 4/2011 | |
| WO | WO 2011/153129 | 12/2011 | |
| WO | WO 2011/153138 | 12/2011 | |
| WO | WO 2012/171016 | 12/2012 | |
| WO | WO 2014/205354 A2 | 12/2014 | |

* cited by examiner

Figure 1-A
XRPD of the Mesylate Salt Crystal
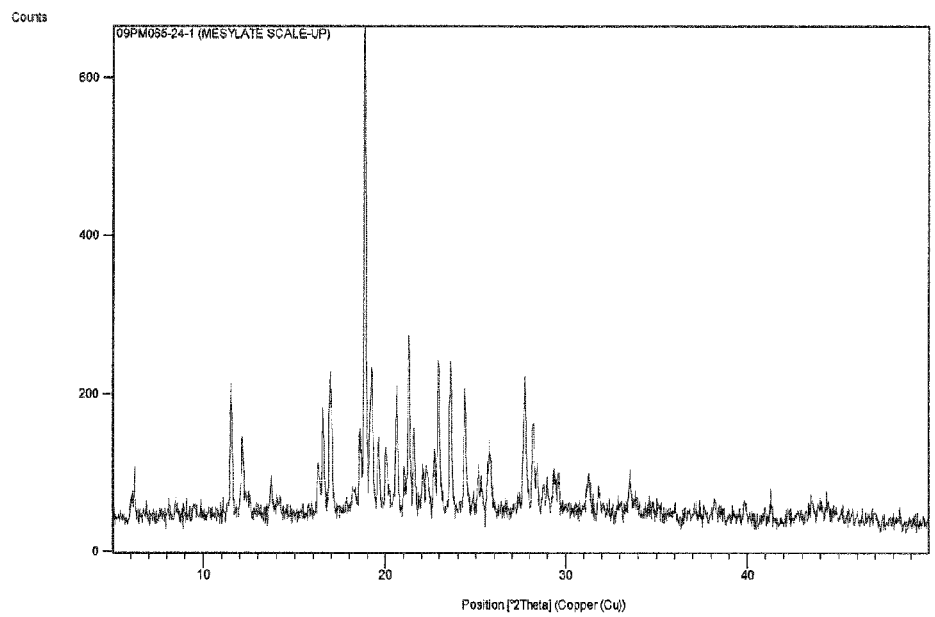
Figure 1-B
Differential Thermal Analysis (DTA) of the Mesylate Salt Crystals
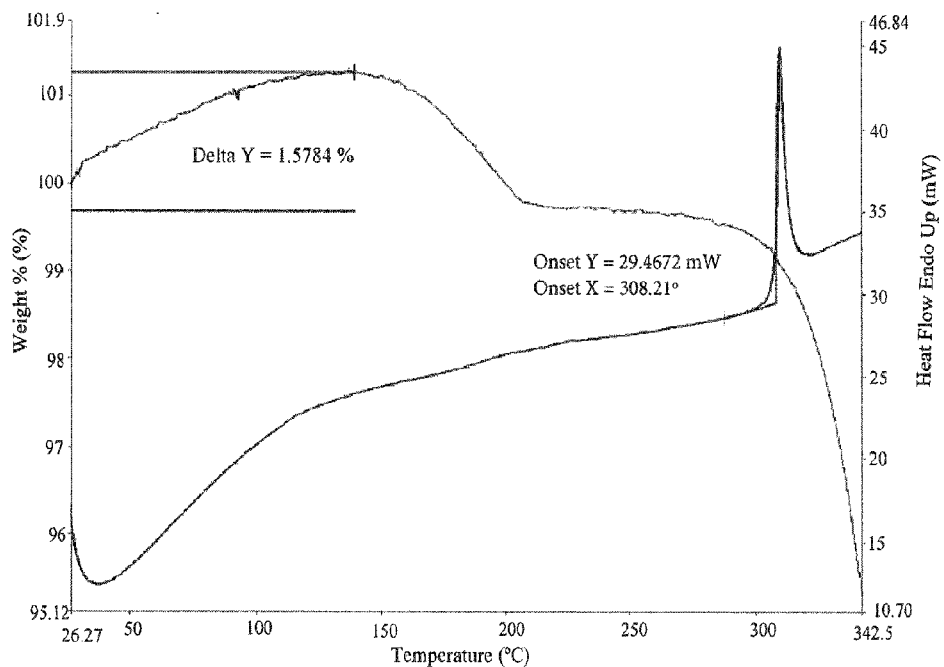

Figure 2-A
XRPD of the Fumarate Salt Crystals
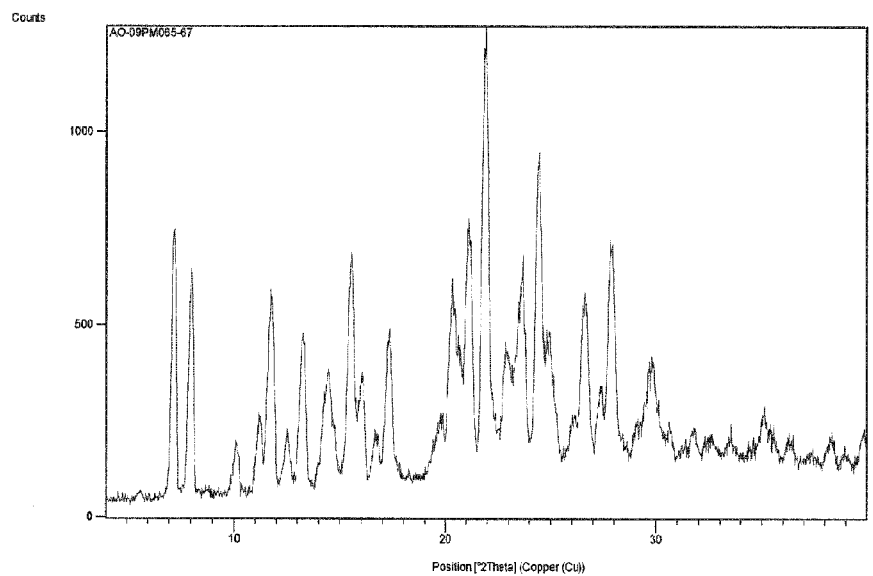
Figure 2-B
Differential Scanning Calorimetry (DSC) thermograph of the Fumarate Salt Crystals
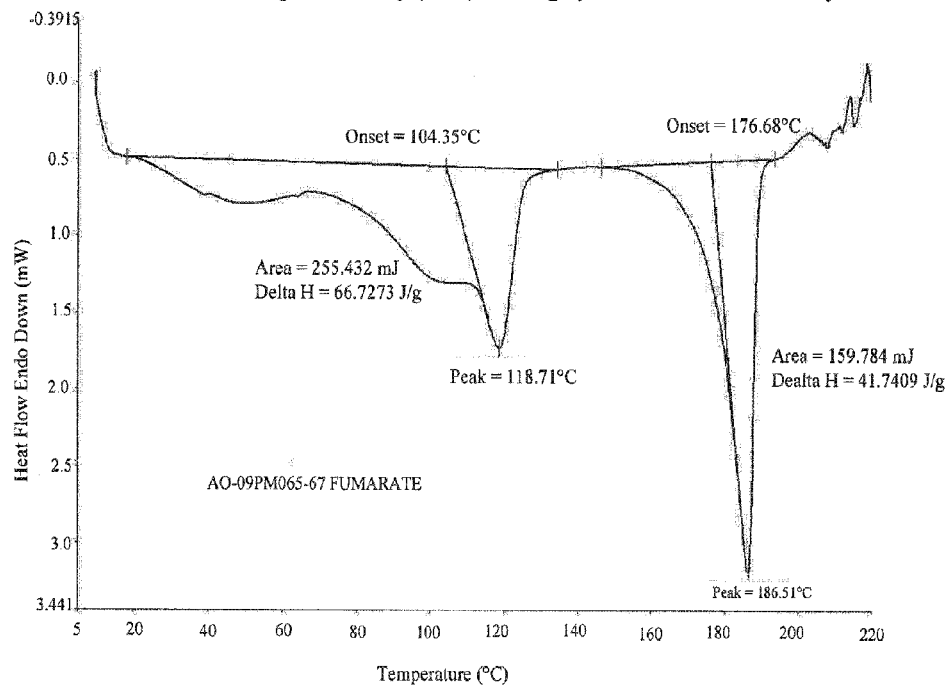

Figure 3-A
XRPD of the Mono-Phosphate Salt Crystals
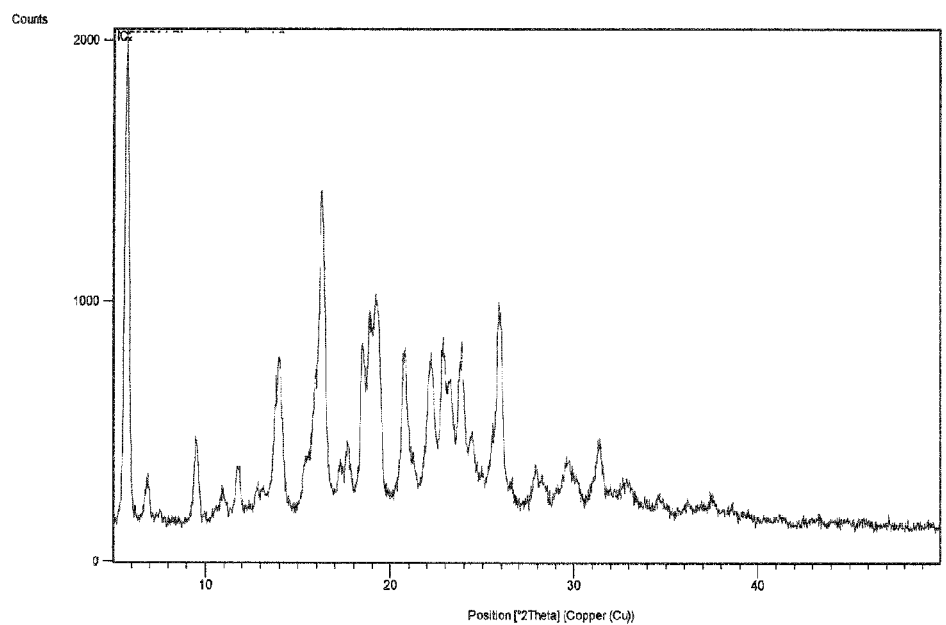
Figure 3-B
TGA analysis of the Mono-Phosphate Salt Crystals
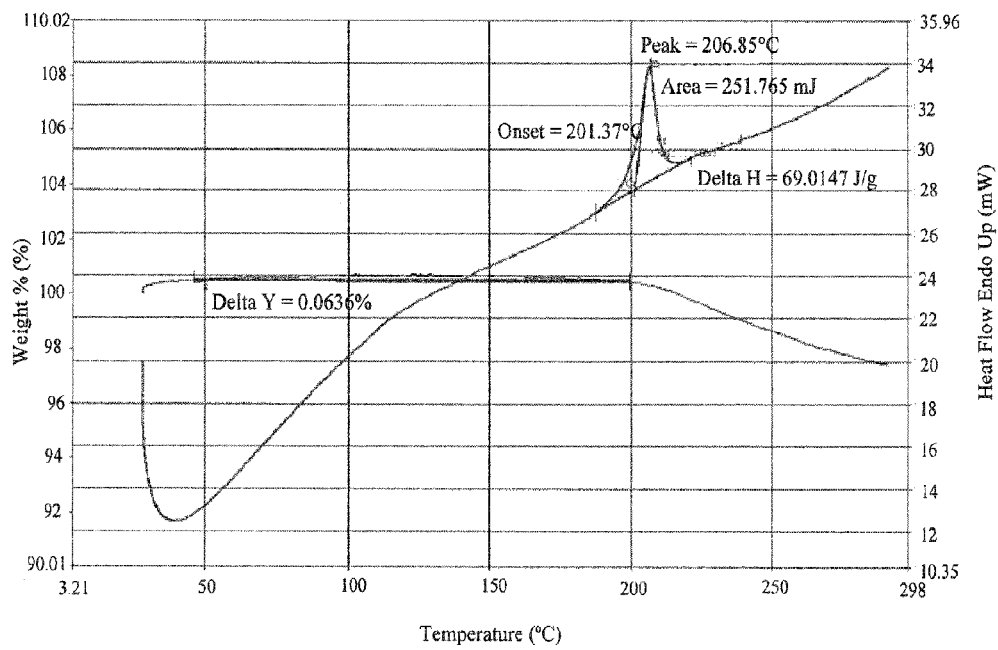

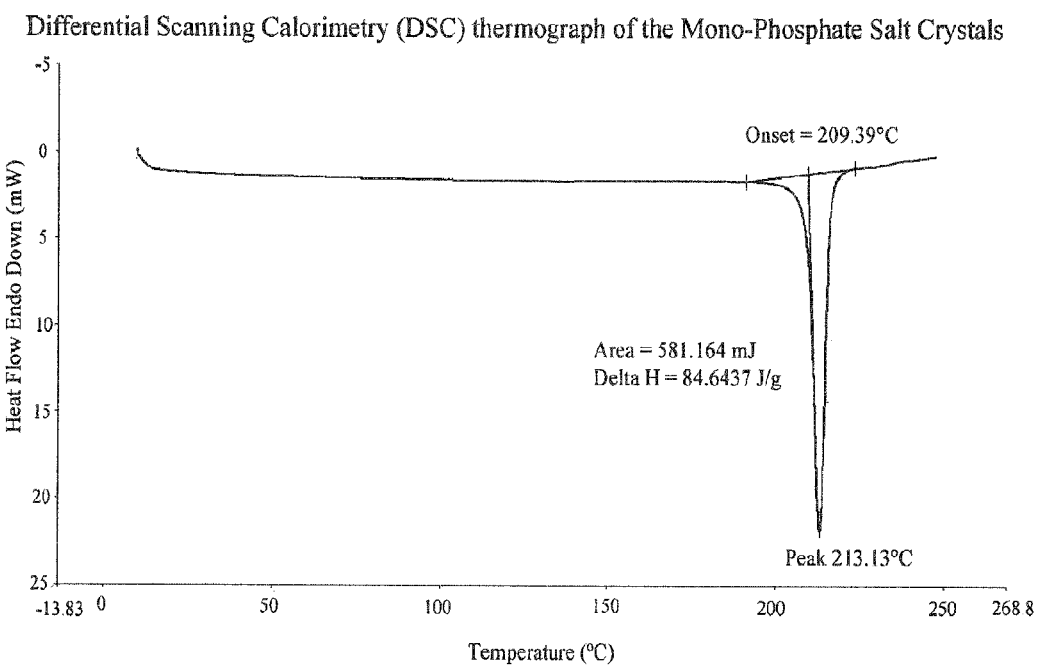
Figure 3-C

Figure 4-A
XRPD of the L-Tartrate Salt Crystals
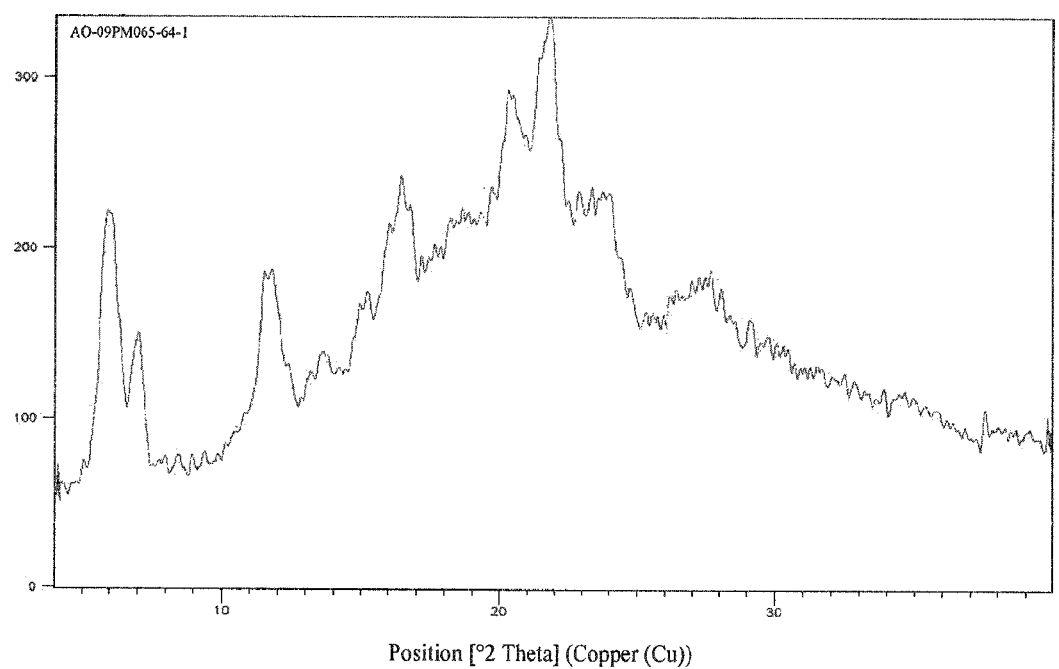
Position [°2 Theta] (Copper (Cu))

Figure 5-A
Dissolution profiles at pH 1.
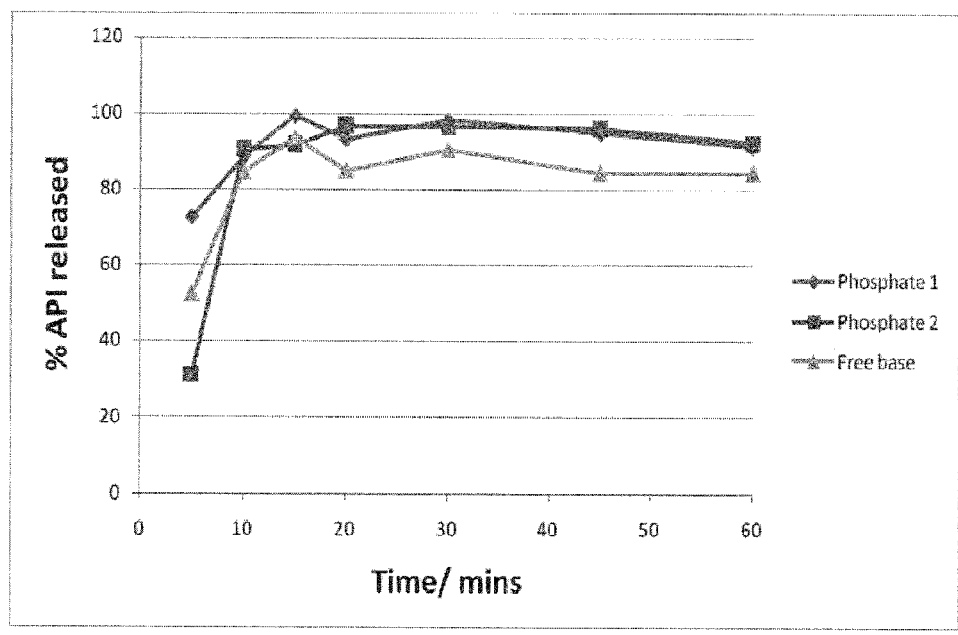
Figure 5-B
Dissolution profiles at pH 4.5.
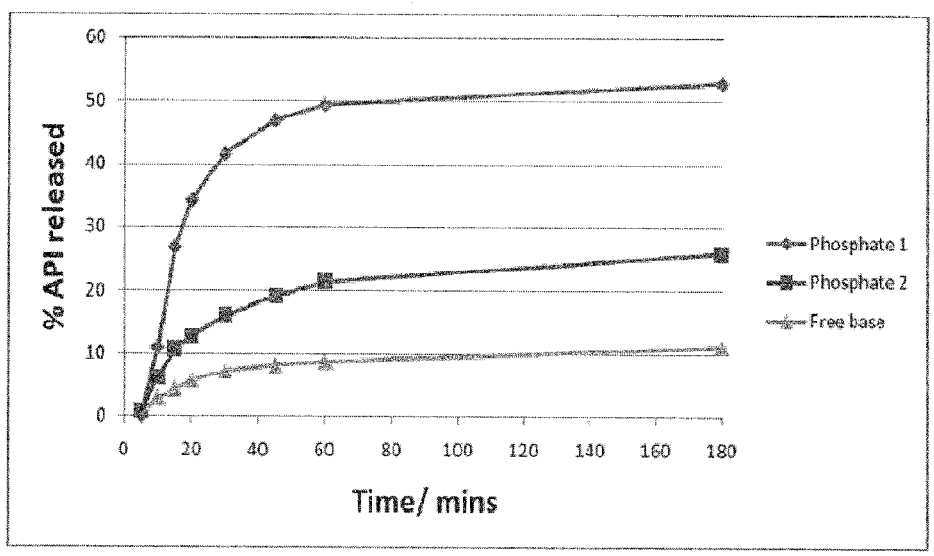

SALT CRYSTALS

CROSS-REFERENCE TO RELATED PATENT APPLICATIONS

This application is a U.S. national phase application filed under 35 U.S.C. §371, claiming the benefit of PCT/US2013/047123 filed on Jun. 21, 2013 which PCT application claims priority from U.S. Prov. Appl. No. 61/662,355, filed on Jun. 21, 2012, the contents of each of which are incorporated by reference in their entirety.

FIELD OF THE INVENTION

The present invention relates to acid addition salts and salt crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4 (2H)-one, composition comprising the same and the method of making and using such salts and salt crystals.

BACKGROUND OF THE INVENTION

The compound (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one is disclosed in WO 2009/075784 (U.S. Pub. No. 2010/0273754). This compound has been found to be a potent and selective phosphodiesterase 1 (PDE 1) inhibitor useful for the treatment or prophylaxis of disorders characterized by low levels of cAMP and/or cGMP in cells expressing PDE1, and/or reduced dopamine D1 receptor signaling activity (e.g., Parkinson's disease, Tourette's Syndrome, Autism, fragile X syndrome, ADHD, restless leg syndrome, depression, cognitive impairment of schizophrenia, narcolepsy); and/or any disease or condition that may be ameliorated by the enhancement of progesterone signaling. This list of disorders is exemplary and not intended to be exhaustive.

The publication WO 2009/075784 discloses (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in free base form and generally in pharmaceutically acceptable salt form, but no specific salt was shown to have particular stability or desired properties. Because many pharmaceutical compounds can exist in different physical forms (e.g., liquid or solid in different crystalline, amorphous, polymorphous, hydrate or solvate forms) which can vary the stability, solubility, bioavailability or pharmacokinetics (absorption, distribution, metabolism, excretion or the like) and/or bioequivalency of a drug, it is of critical importance in the pharmaceutical development to identify a pharmaceutical compound of optimal physical form (e.g., free base or salt in solid, liquid, crystalline, hydrate, solvate, amorphous or polymorphous forms).

SUMMARY OF THE INVENTION

Using twelve acids and eight different solvent systems, our scientists have surprisingly found that (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one forms stable acid addition salts and in certain instances, forms crystallinic acid addition salts with particular acids. These salts and salt crystals are especially advantageous in the preparation of galenic formulations of various and diverse kind. Therefore, in the first aspect, the invention provides the following:

1.1 The compound (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in an acid addition salt form, e.g., selected from the group consisting of fumarate, hydrochloric, (1-hydroxy-2)-naphthoate, benzosulfonate, phosphate, mesylate, tartrate, sulphate and hydrobromate salt;

1.2 The salt according formula 1.1, wherein the salt is a fumarate salt;

1.3 The salt according formula 1.1 or 1.2, wherein the salt is a hemi-fumarate salt;

1.4 The salt according formula 1.1, wherein the salt is a phosphate salt;

1.5 The salt according formula 1.1, wherein the salt is a (1-hydroxy-2)-naphthoate salt;

1.6 The salt according formula 1.1, wherein the salt is a mesylate salt form.

The salt according to any of formulae 1.1-1.6 is referred herein as the Salt(s) of the Present Invention.

It has also been surprisingly found that particular Salts of the Present Invention are in crystalline form, and therefore are preferred for galenic and/or therapeutic use. Therefore, in the second embodiment, the invention provides the following:

1.7 The Salt according to any of claims 1.2-1.6, in crystalline form (hereinafter "Salt Crystals");

1.8 The Salt Crystals according to formula 1.7, wherein the salt crystals are mesylate salt crystals;

1.9 The Salt Crystals according to formula 1.7 or 1.8, wherein the salt crystals are mono-mesylate salt crystals;

1.10 The Salt Crystals according to formula 1.9, wherein said salt crystals are in plate-like form;

1.11 The Salt Crystals according to any of formulae 1.7-1.10, wherein the Salt Crystals exhibit an X-ray powder diffraction pattern comprising at least five peaks having 2-theta angle values selected from the the group consisting of: 11.5, 12.1, 16.5, 16.9, 18.2, 18.9, 19.2, 19.6, 20.6, 21.3, 21.6, 22.9, 23.6, 24.4, 25.7, 27.7, 28.2 and 31.3 degrees, wherein the XRPD pattern is measured in a diffractometer using copper anode, e.g., at wavelength alpha1 of 1.5406 Å and wavelength alpha2 of 1.5444 Å.

1.12 The Salt Crystals according to any of formulae 1.7-1.10, wherein the salt crystals exhibit an X-ray powder diffraction pattern comprising at least five peaks having 2-theta angle values selected from those set forth in Table 1 below:

TABLE 1

| No. | Pos. [°2Th.] | d-spacing [Å] | Height [cts] | Rel. Int. [%] |
|---|---|---|---|---|
| 1 | 6.2157 | 14.21989 | 62.67 | 10.42 |
| 2 | 8.508 | 10.39309 | 23.98 | 7.97 |
| 3 | 11.5155 | 7.68457 | 166.19 | 27.62 |
| 4 | 12.1461 | 7.28702 | 101.68 | 16.9 |
| 5 | 13.6878 | 6.4695 | 50.11 | 11.1 |
| 6 | 16.5424 | 5.35898 | 127.34 | 24.69 |
| 7 | 16.9484 | 5.23151 | 173.1 | 47.95 |
| 8 | 18.2217 | 4.86872 | 39.94 | 15.49 |
| 9 | 18.8543 | 4.70677 | 601.72 | 100 |
| 10 | 19.2322 | 4.61511 | 190.68 | 36.97 |
| 11 | 19.6408 | 4.52002 | 99.09 | 19.21 |
| 12 | 20.0438 | 4.43004 | 89.5 | 14.87 |
| 13 | 20.622 | 4.30713 | 163.42 | 31.69 |

TABLE 1-continued

| No. | Pos. [°2Th.] | d-spacing [Å] | Height [cts] | Rel. Int. [%] |
|---|---|---|---|---|
| 14 | 21.0544 | 4.21963 | 64.38 | 10.7 |
| 15 | 21.2987 | 4.17178 | 233.06 | 45.19 |
| 16 | 21.5693 | 4.12006 | 97.93 | 16.27 |
| 17 | 22.3027 | 3.98621 | 64.13 | 10.66 |
| 18 | 22.9384 | 3.87715 | 203.35 | 33.79 |
| 19 | 23.6005 | 3.76986 | 200.49 | 38.87 |
| 20 | 24.3943 | 3.64896 | 166.22 | 36.83 |
| 21 | 25.1343 | 3.54318 | 63.44 | 10.54 |
| 22 | 25.7457 | 3.4604 | 86.69 | 33.62 |
| 23 | 27.7409 | 3.21589 | 161.76 | 44.8 |
| 24 | 28.1961 | 3.165 | 124.98 | 20.77 |
| 25 | 28.4217 | 3.14039 | 72.04 | 11.97 |
| 26 | 29.3803 | 3.04007 | 61.55 | 13.64 |
| 27 | 29.63 | 3.01502 | 51.92 | 8.63 |
| 28 | 31.2576 | 2.86164 | 57.53 | 15.94 |
| 29 | 31.8561 | 2.80923 | 37.43 | 8.29 |
| 30 | 33.5437 | 2.67166 | 53.93 | 8.96 |
| 31 | 38.3245 | 2.34867 | 14.95 | 9.94 |
| 32 | 39.8831 | 2.2604 | 21.08 | 5.84 |
| 33 | 41.2865 | 2.18675 | 24.75 | 5.48 |
| 34 | 43.5089 | 2.07835 | 27.04 | 14.81 | wherein the XRPD pattern is measured in a diffractometer using copper anode, at wavelength alpha1 of 1.5406 Å and wavelength alpha2 of 1.5444 Å;

1.13 The Salt Crystals according to any of formulae 1.7-1.12, wherein said salt crystals exhibit an X-ray powder diffraction pattern comprising at least five peaks having d-spacing values selected from the group consisting of 7.68, 7.28, 5.36, 5.23, 4.87, 4.71, 4.62, 4.52, 4.31, 4.17, 4.12, 3.88, 3.77, 3.65, 3.46, 3.22, 3.17 and 2.86 Å;

1.14 The Salt Crystals according to any of formulae 1.7-1.12, wherein said salt crystals exhibit an X-ray powder diffraction pattern comprising at least five peaks having d-spacing values selected from those set forth in Table 1 of formula 1.12;

1.15 The Salt Crystals according to any of formulae 1.7-1.14, wherein said salt crystals exhibit an X-ray powder diffraction pattern corresponding with or substantially as set forth in Table 1 of formula 1.12;

1.16 The Salt Crystals according to any of formulae 1.7-1.15, wherein said salt crystals exhibit an X-ray powder diffraction pattern corresponding with or substantially as depicted in FIG. 1-A;

1.17 The Salt Crystals according to any of formulae 1.7-1.16, wherein said salt crystals exhibit a Differential Thermal Analysis (DTA) pattern comprising a peak with an endotherm onset at about 308° C.;

1.18 The Salt Crystals according to any of formulae 1.7-1.17, wherein said salt crystals exhibit a Differential Thermal Analysis (DTA) pattern corresponding with or substantially as depicted in FIG. 1-B;

1.19 The Salt Crystals according to any of formulae 1.7-1.18, wherein said salt crystals exhibit a plate-like morphology;

1.20 The Salt Crystals according to any of formulae 1.7-1.19, wherein said salt crystals are prepared by reacting (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in methanol with methanesulfonic acid in water, optionally adding diethyl ether as anti-solvent;

1.21 The Salt Crystals according to formula 1.7, wherein the salt crystals are fumarate salt crystals;

1.22 The Salt Crystals according to formula 1.7 or 1.21, wherein the salt crystals are hemi-fumarate salt crystals;

1.23 The Salt Crystals according to any of formulae 1.7 or 1.21-1.22, wherein the salt crystals are mono-fumarate salt crystals;

1.24 The Salt Crystals according to any of formulae 1.7 or 1.21, wherein the salt crystals exhibit a needle-like morphology;

1.25 The Salt Crystals according to any of formulae 1.7, 1.21 or 1.24, wherein the salt crystals are in non-solvate form;

1.26 The Salt Crystals according to any of formulae 1.7, 1.21, or 1.24-1.25, wherein said salt crystals exhibit an X-ray powder diffraction pattern comprising at least five peaks having 2-theta angle values selected from the group consisting of 7.2, 8.0, 10.1, 11.2, 11.7, 12.5, 13.2, 14.4, 15.5, 16.0, 16.7, 17.3, 19.8, 20.3, 21.1, 21.9, 22.9, 23.6, 24.4, 24.9, 26.1, 26.6, 27.4, 27.9, 29.0, 29.8, 31.8, 32.6, 33.5, 35.1, 36.3, 38.3 and 39.0 degrees, wherein the XRPD pattern is measured in a diffractometer using copper anode, e.g., at wavelength alpha1 of 1.5406 Å and wavelength alpha2 of 1.5444 Å;

1.27 The Salt Crystals according to any of formulae 1.7, 1.21, or 1.24-1.26, wherein said salt crystals exhibit an X-ray powder diffraction pattern comprising at least five peaks having 2-theta angle values selected from those set forth in Table 2 below:

TABLE 2

| No. | Pos. [°2Th.] | d-spacing [Å] | Height [cts] | Rel. Int. [%] |
|---|---|---|---|---|
| 1 | 5.5976 | 15.78845 | 15.13 | 1.4 |
| 2 | 7.2032 | 12.27251 | 697.12 | 70.13 |
| 3 | 8.0142 | 11.03222 | 583.28 | 36.11 |
| 4 | 10.1187 | 8.742 | 138.56 | 17.16 |
| 5 | 11.1976 | 7.90199 | 218.18 | 30.39 |
| 6 | 11.7461 | 7.53423 | 525.96 | 81.4 |
| 7 | 12.5036 | 7.07943 | 168.07 | 15.61 |
| 8 | 13.2367 | 6.68895 | 407.76 | 34.71 |
| 9 | 14.1892 | 6.24199 | 232.02 | 10.77 |
| 10 | 14.4233 | 6.1412 | 329.19 | 20.38 |
| 11 | 14.7399 | 6.01002 | 188.07 | 11.64 |
| 12 | 15.5157 | 5.71122 | 639.38 | 29.69 |
| 13 | 16.0172 | 5.53349 | 316.16 | 34.25 |
| 14 | 16.6971 | 5.30968 | 158.43 | 19.62 |
| 15 | 17.322 | 5.11951 | 442.23 | 20.53 |
| 16 | 19.7866 | 4.48704 | 203.55 | 18.9 |
| 17 | 20.3297 | 4.36838 | 555.19 | 51.56 |
| 18 | 21.1031 | 4.21 | 689.14 | 95.99 |
| 19 | 21.9181 | 4.05526 | 1199.87 | 83.57 |
| 20 | 22.9016 | 3.8833 | 375.79 | 34.9 |
| 21 | 23.6407 | 3.76354 | 577.36 | 62.55 |
| 22 | 24.4164 | 3.64569 | 872.48 | 54.01 |
| 23 | 24.9125 | 3.57422 | 422.71 | 52.34 |
| 24 | 26.1016 | 3.41403 | 212.31 | 23 |
| 25 | 26.6168 | 3.3491 | 527.74 | 89.85 |
| 26 | 27.3903 | 3.25625 | 278.33 | 21.54 |
| 27 | 27.8762 | 3.20059 | 646.12 | 100 |
| 28 | 29.0497 | 3.07391 | 179.56 | 16.67 |
| 29 | 29.8276 | 2.9955 | 349.25 | 27.03 |
| 30 | 30.6371 | 2.91817 | 187.24 | 14.49 |
| 31 | 31.7612 | 2.81741 | 173.36 | 16.1 |
| 32 | 32.5634 | 2.74981 | 155.03 | 19.2 |
| 33 | 33.5077 | 2.67444 | 161.64 | 15.01 |
| 34 | 35.0864 | 2.55764 | 222.69 | 24.13 |
| 35 | 36.3098 | 2.47422 | 149.42 | 23.13 |
| 36 | 38.2838 | 2.34912 | 154.74 | 47.37 |
| 37 | 38.9662 | 2.31528 | 116.83 | 23.84 | wherein the XRPD pattern is measured in a diffractometer using copper anode, at wavelength alpha1 of 1.5406 Å and wavelength alpha2 of 1.5444 Å;

1.28 The Salt Crystals according to any of formulae 1.7, 1.21, or 1.24-1.27, wherein the salt crystals exhibit an X-ray powder diffraction pattern comprising at least five peaks having d-spacing values selected from the group consisting of 12.27, 11.03, 8.74, 7.90, 7.53, 7.08, 6.69, 6.14, 5.71, 5.53, 5.31, 5.12, 4.49, 4.37, 4.21, 4.06, 3.88, 3.76, 3.45, 3.57, 3.41, 3.35, 3.26, 3.20, 3.07, 3.00, 2.82, 2.75, 2.67, 2.56, 2.47, 2.35 and 2.32 Å;

1.29 The Salt Crystals according to any of formulae 1.7, 1.21, or 1.24-1.28, wherein the salt crystals exhibit an X-ray powder diffraction pattern comprising at least five peaks having d-spacing values selected from those set forth in Table 2 of formula 1.27;

1.30 The Salt Crystals according to any of formulae 1.7, 1.21, or 1.24-1.29, wherein the salt crystals exhibit an X-ray powder diffraction pattern corresponding with or substantially as set forth in Table 2 of formula 1.27;

1.31 The Salt Crystals according to any of formulae 1.7, 1.21, or 1.24-1.30, wherein the salt crystals exhibit an X-ray powder diffraction pattern corresponding with or substantially as depicted in FIG. 2-A;

1.32 The Salt Crystals according to any of formulae 1.7, 1.21, or 1.24-1.31, wherein the salt crystals exhibit a Differential Scanning Calorimetry (DSC) pattern comprising a peak with an endotherm at about 176° C.;

1.33 The Salt Crystals according to formula 1.32, wherein the salt crystals exhibit a Differential Scanning Calorimetry (DSC) pattern corresponding with or substantially as depicted in FIG. 2-B;

1.34 The Salt Crystals according to any of formulae 1.7 or 1.21-1.25, wherein the salt crystals are in hydrate form;

1.35 The Salt Crystals according to any of formulae 1.7 or 1.21-1.25, wherein the salt crystals are in non-hydrate form;

1.36 The Salt Crystals according to any of formulae 1.7 or 1.21-1.35, wherein the salt crystals are prepared by reacting (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in methanol with fumaric acid (e.g., 1 molar equivalence) optionally in the presence of heat;

1.37 The Salt Crystals according to formula 1.7, wherein the salt crystals are L-tartrate salt crystals;

1.38 The Salt Crystals according to formula 1.7 or 1.37, wherein the salt crystals exhibit an X-ray powder diffraction pattern comprising at least five peaks having 2-theta angle values selected from those depicted in FIG. 4-A;

1.39 The Salt Crystals according to any of formulae 1.7 or 1.37-1.38, wherein the salt crystals exhibit an X-ray powder diffraction pattern corresponding with or substantially as depicted in FIG. 4-A;

1.40 The Salt Crystals according to any of formulae 1.7 or 1.37-1.39, wherein said salt crystals are prepared by reacting (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in acetone with L-tartaric acid;

1.41 The Salt Crystals according to formula 1.7, wherein the salt crystals are phosphate salt crystals;

1.42 The Salt Crystals according to formula 1.7 or 1.41, wherein the salt crystals are mono-phosphate salt crystals;

1.43 The Salt Crystals according to any of formulae 1.7 or 1.41-1.43, wherein the salt crystals are in a non-solvate form;

1.44 The Salt Crystals according to formula 1.7, 1.41-1.43, wherein the salt crystals are in a non-hydrate form;

1.45 The Salt Crystals according to any of formulae 1.7 or 1.41-1.44, wherein the crystals are in a dry (non-solvate and non-hydrate) form;

1.46 The Salt Crystals according to any of formulae 1.7 or 1.41-1.45, wherein the salt crystals are in mono-phosphate, non-solvate, non-hydrate salt form;

1.47 Salt Crystals according to any of formulae 1.7 or 1.41-1.46, wherein the Salt Crystals exhibit an X-ray powder diffraction pattern comprising one or more peaks having 2-theta angle values selected from the group consisting of 13.8, 16.3, 19.2, 23.2, 23.8 and 25.9 degrees, wherein the XRPD pattern is measured in a diffractometer using copper anode, e.g., at wavelength alpha1 of 1.5406 Å and wavelength alpha2 of 1.5444 Å. In another embodiment, the Salt Crystals exhibit an X-ray powder diffraction pattern comprising at least five peaks having 2-theta angle values selected from the group consisting of 9.5, 13.8, 14.0, 16.3, 17.7, 18.5, 18.9, 19.2, 22.2, 22.8, 23.2, 23.8, 24.4, 25.9, 29.7, 31.4 and 32.9 degrees, wherein the XRPD pattern is measured in a diffractometer using copper anode, e.g., at wavelength alpha1 of 1.5406 Å and wavelength alpha2 of 1.5444 Å;

1.48 Salt Crystals according to any of formulae 1.7 or 1.41-1.46, wherein the Salt Crystals exhibit an X-ray powder diffraction pattern comprising at least five peaks having 2-theta angle values selected from those set forth in Table 3 below:

TABLE 3

| No. | Pos. [°2Th.] | d-spacing [Å] | Height [cts] | Rel. Int. [%] |
| --- | --- | --- | --- | --- |
| 1 | 5.7553 | 15.35618 | 1887.34 | 73.85 |
| 2 | 6.8867 | 12.8358 | 176.68 | 10.75 |
| 3 | 7.5188 | 11.75808 | 53.19 | 2.78 |
| 4 | 9.4821 | 9.32747 | 328.23 | 22.83 |
| 5 | 10.9511 | 8.07934 | 133.75 | 4.65 |
| 6 | 11.7509 | 7.53118 | 226.95 | 7.89 |
| 7 | 11.8625 | 7.46054 | 201.05 | 5.24 |
| 8 | 12.7859 | 6.92377 | 149.08 | 6.48 |
| 9 | 13.7504 | 6.44022 | 456.19 | 15.87 |
| 10 | 13.9906 | 6.33014 | 633 | 44.04 |
| 11 | 15.3855 | 5.75923 | 245.11 | 12.79 |
| 12 | 16.2789 | 5.44515 | 1277.75 | 100 |
| 13 | 17.2688 | 5.13515 | 241.96 | 10.52 |
| 14 | 17.6964 | 5.01205 | 312.05 | 18.99 |
| 15 | 18.5004 | 4.796 | 690.64 | 36.03 |
| 16 | 18.8841 | 4.6994 | 800.41 | 27.84 |
| 17 | 19.2158 | 4.61904 | 859.15 | 74.71 |
| 18 | 20.6821 | 4.29474 | 559.5 | 14.6 |
| 19 | 22.2013 | 4.00417 | 641.59 | 50.21 |
| 20 | 22.8385 | 3.89388 | 682.56 | 41.55 |
| 21 | 23.2185 | 3.83102 | 555.61 | 24.16 |
| 22 | 23.8425 | 3.73215 | 697.52 | 54.59 |
| 23 | 24.4086 | 3.64685 | 357.59 | 18.66 |
| 24 | 25.8905 | 3.44137 | 842.43 | 29.3 |
| 25 | 27.9329 | 3.19423 | 221.79 | 11.57 |
| 26 | 29.6611 | 3.01192 | 250.43 | 26.13 |
| 27 | 31.3753 | 2.85118 | 306.23 | 15.98 |
| 28 | 32.863 | 2.72542 | 167.88 | 20.44 |
| 29 | 34.6203 | 2.591 | 111.05 | 7.73 |
| 30 | 36.2262 | 2.47975 | 92.41 | 4.82 |
| 31 | 37.5261 | 2.39678 | 105.94 | 6.45 |
| 32 | 41.1361 | 2.19441 | 25.77 | 4.03 |
| 33 | 45.786 | 1.98015 | 21.45 | 4.92 | wherein the XRPD pattern is measured in a diffractometer using copper anode, at wavelength alpha1 of 1.5406 Å and wavelength alpha2 of 1.5444 Å;

1.49 Salt Crystals according to any of formulae 1.7 or 1.41-1.48, wherein the Salt Crystals exhibit an X-ray powder diffraction pattern comprising one or more peaks having d-spacing values selected from the group consisting of 6.44, 5.45, 4.62, 3.83, 3.73 and 3.44 Å. In another embodiment, the invention provides Salt Crystals according to any of formulae 1.7 or 1.41-1.48, wherein the Salt Crystals exhibit an X-ray powder diffraction pattern comprising at least five peaks having d-spacing values selected from the group consisting of 15.36, 9.33, 6.44, 6.33, 5.45, 5.01, 4.80, 4.70, 4.62, 4.00, 3.89, 3.83, 3.73, 3.65, 3.44, 3.01, 2.85 and 2.73 Å;

1.50 Salt Crystals according to any of formulae 1.7 or 1.41-1.48, wherein the Salt Crystals exhibit an X-ray powder diffraction pattern comprising at least five peaks having d-spacing values selected from those set forth in Table 3 of formula 1.48;

1.51 Salt Crystals of the Invention or any of formulae 1.7 or 1.41-1.48, wherein the Salt Crystals exhibit an X-ray powder diffraction pattern corresponding with or substantially as herein set forth in Table 3 of formula 1.48;

1.52 Salt Crystals of the Invention or any of formulae 1.7 or 1.41-1.49, wherein said Salt Crystals exhibit an X-ray powder diffraction pattern corresponding with or substantially as herein depicted in FIG. 3-A;

1.53 Salt Crystals of the Invention or any of formulae 1.7 or 1.41-1.52, wherein said Salt Crystals exhibit a Thermogravimetic Analysis (TGA) data pattern comprising a peak at about 206° C.;

1.54 Salt Crystals of the Invention or any of formulae 1.7 or 1.41-1.53, wherein the Salt Crystals exhibit a thermogravimetic analysis pattern corresponding with or substantially as depicted in FIG. 3-B;

1.55 Salt Crystals of the Invention or any of formulae 1.7 or 1.41-1.54, wherein the salt crystals are prepared by reacting the compound (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in acetonitrile with phosphoric acid (e.g., 1 molar equivalent), e.g., phosphoric acid hydrate or phosphoric acid crystal in acetonitrile, optionally in the presence of heat;

1.56 The Salt Crystals according to any of formulae 1.7 or 1.41-1.55, wherein the salt crystals are in plate-like form;

1.57 The Salt Crystals according to any of formulae 1.7 or 1.41-1.56, wherein the salt crystals exhibit a Differential Thermal Analysis (DTA) pattern comprising a peak with a melting temperature at about 202°-212° C., e.g., about 207° C.-208° C.;

1.58 The Salt Crystals according to any of formulae 1.7 or 1.41-1.57, wherein the salt crystals exhibit a Differential Thermal Analysis (DTA) pattern corresponding with or substantially as herein depicted in FIG. 3-B;

1.59 The Salt Crystals according to any of formulae 1.7 or 1.41-1.58, wherein the salt crystals exhibit a Differential Scanning Calorimetry (DSC) comprising a peak with an endotherm at about 213° C.;

1.60 The Salt Crystals according to any of formulae 1.7 or 1.41-1.59, wherein the salt crystals exhibit a Differential Scanning Calorimetry (DSC) pattern corresponding with or substantially as herein depicted in FIG. 3-C;

1.61 Salt Crystals according to any of the above formulae, wherein said Salt Crystals are in a single crystal form and are free or substantially free of any other form, e.g., less than 10 wt. %, preferably less than about 5 wt. %, more preferably less than about 2 wt. %, still preferably less than about 1 wt. %, still preferably less than about about 0.1%, most preferably less than about 0.01 wt. % of amorphous form;

1.62 Salt Crystals according to any of the above formulae, wherein said Salt Crystals are in a single crystal form and are free or substantially free of any other form, e.g., less than 10 wt. %, preferably less than about 5 wt. %, more preferably less than about 2 wt. %, still preferably less than about 1 wt. %, still preferably less than about about 0.1%, most preferably less than about 0.01 wt. % of other crystal forms;

1.63 Salt Crystals according to any of the above formulae, wherein said Salt Crystals are in a single crystal form and are free or substantially free of any other form, e.g., less than 10 wt. %, preferably less than about 5 wt. %, more preferably less than about 2 wt. %, still preferably less than about 1 wt. %, still preferably less than about about 0.1%, most preferably less than about 0.01 wt. % of amorphous and other crystal forms;

1.64 Salt Crystals of the Invention when made by any of processes described or similarly described in any of formulae 2.1-2.20 or any of Examples 1-4.

The invention also provides a process for the production of Salt of the Invention, e.g., selected from the group consisting of fumarate, hydrochloric, (1-hydrox-2)-naphthoate, benzosulfonate, phosphate, mesylate, tartrate, sulphate and hydrobromate salt crystals, comprising the steps of reacting (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4 (2H)-one with an acid, e.g., selected from the group consisting of fumaric acid, hydrochloric acid, (1-hydroxy-2)-naphthoic acid, benzenesulfonic acid, phosphoric acid, methanesulphonic acid, tartaric acid, sulphuric acid and hydrobromic acid in a solvent and isolating the salt obtained. Preferably, the salt is a phosphate salt and the acid is phosphoric acid, e.g., aqueous phosphoric acid, phosphoric acid hydrate or phosphoric acid crystal in a solvent. In a particular embodiment, the invention provides the following:

2.1 A process for the production of Salt Crystals of the Invention, e.g., phosphate salt crystals of the invention, comprising the steps of reacting (6aR,9aS)-5,6a,7,8,9, 9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one with phosphoric acid, e.g., aqueous phosphoric acid, phosphoric acid hydrate or phosphoric acid crystal in a solvent;

2.2 The process according to formula 2.1, wherein the phosphoric acid is in the amount of about 1 molar equivalent of phosphoric acid to one molar equivalent of the free base;

2.3 The process according to formula 2.1, wherein the phosphoric acid is in the amount of about 0.5 molar equivalent of phosphoric acid to one molar equivalent of the free base;

2.4 The process according to formula 2.1, 2.2 or 2.3, wherein the solvent is selected from acetonitrile and methanol;

2.5 The process according to any of formulae 2.1-2.4, wherein the solvent is acetonitrile;

2.6 The process according to any of formulae 2.5, wherein the free base is dissolved in the solvent acetonitrile;

2.7 The process according to any of formulae 2.1-2.6, wherein the mixture/solution of free base in acetonitrile is further heated to an elevated temperature (e.g., to a temperature of about 40° C., e.g., until all solids are dissolved);

2.8 The process according to formula 2.6 or 2.7, wherein the ratio of acetonitrile to free base is about 11 mL of acetonitrile to 1 mg of free base;

2.9 The process according to any of formulae 2.1-2.8, wherein the phosphoric acid is an aqueous phosphoric acid, phosphoric acid hydrate or phosphoric acid crystal;

2.10 The process according to any of formulae 2.1-2.9, wherein the phosphoric acid, e.g., 85 wt. % phosphoric acid hydrate or phosphoric acid crystal, is dissolved in acetonitrile;

2.11 The process according to any of formulae 2.1-2.10, wherein the ratio of acetonitrile used to dissolve the phosphoric acid is in the amount of about 2 mL of acetonitrile to 1 g of free base, e.g., 1.8 mL of acetonitrile to 1 g of free base;

2.12 The process according to any of formulae 2.1-2.11, wherein the reaction mixture/solution is optionally subjected to temperature cycling (e.g., 40° C./RT);

2.13 The process according to any of formulae 2.1-2.12, wherein the process optionally involves the addition of an anti-solvent;

2.14 The process according to formula 2.13, wherein the anti-solvent is diethyl ether;

2.15 The process according to any of formulae 2.1-2.12, comprising reacting (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in 11 mL of acetonitrile to 1 mg of free base, with phosphoric acid in the amount of one molar equivalent;

2.16 The process according to formula 2.15, comprising reacting (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in 11 mL of acetonitrile per 1 mg of free base, with 1 molar equivalent of 85 wt. % phosphoric acid hydrate or phosphoric acid crystal in acetonitrile;

2.17 The process according to formula 2.16, wherein the mixture/solution of free base in acetonitrile is further heated to an elevated temperature (e.g., to a temperature of about 40° C., e.g., until all solids dissolved);

2.18 The process according to any of the above formulae, wherein the reaction mixture/solution is optionally sonicated;

2.19 The process according to any of the above formulae, further comprises the step of isolating the crystals thus obtained;

2.20 The process according to any of the above formulae further comprises the step of drying the crystals thus obtained (e.g., in an oven at about 50° C.).

In the third aspect, the invention provides the following:

2.21 A pharmaceutical composition comprising (a) the compound (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in acid addition salt form according to any of formulae 1.1-1.6, or (b) Salt Crystals of the Present Invention, e.g., any of formulae 1.7-1.64, as active ingredient, together with a pharmaceutically acceptable diluent or carrier;

2.22 The pharmaceutical composition comprising the Salt Crystals of the Present Invention, e.g., any of formulae 1.7-1.64, as active ingredient, together with a pharmaceutically acceptable diluent or carrier wherein said composition is predominantly, or is entirely or substantially entirely, in dry crystalline form;

2.23 Salt Crystals of the Present Invention, e.g., any of formulae 1.7-1.64, for use as a pharmaceutical, e.g., for use in method of 2.24-2.2.25, or for use in the manufacture of a medicament for treating an indication as set forth in any of formulae 2.24-2.25;

2.24 A method for the prophylaxis or treatment of a patient, e.g., a human suffering from a disorder selected from the following disorders:
  (i) Neurodegenerative diseases, including Parkinson's disease, restless leg, tremors, dyskinesias, Huntington's disease, Alzheimer's disease, and drug-induced movement disorders;
  (ii) Mental disorders, including depression, attention deficit disorder, attention deficit hyperactivity disorder, bipolar illness, anxiety, sleep disorders, e.g., narcolepsy, cognitive impairment, e.g., cognitive impairment of schizophrenia, dementia, Tourette's syndrome, autism, fragile X syndrome, psychostimulant withdrawal, and drug addiction;
  (iii) Circulatory and cardiovascular disorders, including cerebrovascular disease, stroke, congestive heart disease, hypertension, pulmonary hypertension (e.g., pulmonary arterial hypertension), and sexual dysfunction;
  (iv) Respiratory and inflammatory disorders, including asthma, chronic obstructive pulmonary disease, and allergic rhinitis, as well as autoimmune and inflammatory diseases;
  (v) diseases that may be alleviated by the enhancement of progesterone-signaling such as female sexual dysfunction;
  (vi) a disease or disorder such as psychosis or glaucoma or elevated intraocular pressure;
  (vii) Traumatic brain injury;
  (viii) Any disease or condition characterized by low levels of cAMP and/or cGMP (or inhibition of cAMP and/or cGMP signaling pathways) in cells expressing PDE1; and/or
  (ix) Any disease or condition characterized by reduced dopamine D1 receptor signaling activity,
  comprising administering to a patient in need thereof a therapeutically effective amount of (a) the compound (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in acid addition salt form according to any of formulae 1.1-1.6, or (b) the Salt Crystals of the Present Invention, e.g., any of formulae 1.7-1.64;

2.25 The method of formula 2.24, wherein said disorder is selected from the group consisting of Parkinson's disease, narcolepsy, sleep disorder and cognitive impairment, e.g., cognitive impairment of schizophrenia;

2.26 The method of formula 2.24, wherein said disorder is narcolepsy;

2.27 The method of formula 2.24, wherein said disorder is sleep disorders;

2.28 The method of formula 2.24, wherein said disorder is cognitive impairment;

2.29 The method of formula 2.24, wherein said disorder is cognitive impairment of schizophrenia;

2.30 A pharmaceutical composition according to formula 2.21 for use as a medicament, e.g., for use in the manufacture of a medicament for the treatment or prophylaxis of a disease as described in any of formulae 2.24-2.29.

BRIEF DESCRIPTION OF THE DRAWINGS

FIG. 1-A depicts an X-ray Powder Diffraction pattern of the mesylate Salt Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one.

FIG. 1-B depicts a Differential Thermal Analysis (DTA) of the mesylate Salt Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one.

FIG. 2-A depicts an X-ray Powder Diffraction pattern of the fumarate Salt Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one.

FIG. 2-B depicts a Differential Scanning Calorimetry (DSC) thermograph of the fumarate Salt Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one.

FIG. 3-A depicts an X-ray Powder Diffraction pattern of the mono-phosphate Salt Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one.

FIG. 3-B depicts a TGA analysis of the mono-phosphate Salt Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one.

FIG. 3-C depicts a Differential Scanning Calorimetry (DSC) thermograph of the mono-phosphate Salt Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one.

FIG. 4-A depicts an X-ray Powder Diffraction pattern of the L-Tartrate Salt Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one.

FIG. 5-A depicts the dissolution profiles of the mono-phosphate salt crystals and the amorphous free base of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one at pH 1.

FIG. 5-B depicts the dissolution profiles of the mono-phosphate salt crystals and the amorphous free base of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one at pH 4.5.

DETAIL DESCRIPTION

As use herein, the term "crystal" or "crystals" or "crystalline" or "crystallinic" refers to any solid that has a short or long range order of the molecules, atoms or ions in a fixed lattice arrangement. Salt Crystals of the Present Invention may be in a single crystal form. Therefore, the Salt Crystals of the Present Invention may be in a triclinic, monoclinic, orthorhombic, tetragonal, rhombohedral, hexagonal or cubic crystal form or mixtures thereof. In particular, the Salt Crystals of the Present Invention are in dry crystalline form. In another embodiment, the Salt Crystals of the Present Invention are in needle form. In still another embodiment, the Salt Crystals of the Present Invention are in plate-like form. In a particular embodiment, the Salt Crystals of the Present Invention are substantially free of other forms, e.g., free of amorphous or other crystal forms.

The term "substantially free" of other crystal forms refer to less than about 10 wt. %, preferably less than about 5 wt. %, more preferably less than about 2 wt. %, still preferably less than about 1 wt. %, still preferably less than about about 0.1%, most preferably less than about 0.01 wt. % of other forms or other crystal forms, e.g., amorphous or other crystal forms.

The term "predominantly" or "substantially entirely in a single form" refers to less than about 10 wt. %, preferably less than about 5 wt. %, more preferably less than about 2 wt. %, still preferably less than about 1 wt. %, still preferably less than about about 0.1%, most preferably less than about 0.01 wt. % of other crystal forms, e.g., amorphous or other crystal forms.

In particular embodiment, the Salt Crystals of the invention may contain trace amounts of solvent, e.g., in solvate form, or trace amounts of water, e.g., in hydrate form. Preferably, the Salt Crystals of the invention are in non-solvate form. Still preferably, the Salt Crystals of the invention are in non-solvate and non-hydrate form.

The Salt Crystals of the invention may have a free base to acid ratio of 1 to 1, 1 to 0.5 or 1 to >1, e.g., 1 to 1.3 or 1 to 2, etc. For example, the phosphate salt crystal of the invention may comprise 1 molar equivalent of the free base to 1 molar equivalent of the phosphoric acid. Preferably, the phosphate salt crystal of the invention comprises 1 molar equivalent of the free base to 1 molar equivalent of the phosphoric acid Wherein the acid is a di-acid, such as fumaric acid or tartaric acid, the ratio of free base to acid may be 1 molar equivalent of free base to 0.5 equivalent of the di-acid, e.g., to form a hemi-fumarate or hemi-tartrate salt.

The term "solvate" refers to crystalline solid adducts containing either stoichiometric or nonstoichiometric amounts of a solvent incorporated within the crystal structure. Therefore, the term "non-solvate" form herein refers to salt crystals that are free or substantially free of solvent molecules within the crystal structures of the invention. Similarly, the term "non-hydrate" form herein refers to salt crystals that are free or substantially free of water molecules within the crystal structures of the invention.

The term "amorphous" form refers to solids of disordered arrangements of molecules and do not possess a distinguishable crystal lattice.

The crystallinity or the morphology of the Salt Crystals of the Present Invention may be determined by a number of methods, including, but not limited to single crystal X-ray diffraction, X-ray powder diffraction, polarizing optical microscopy, thermal microscopy, differential scanning Calorimetry (DSC), thermogravimetric analysis (TGA), infrared adsorption spectroscopy and Raman spectroscopy. Characterization of solvates or hydrates or lack thereof may also be determined by DSC and/or TGA.

It is to be understood that X-ray powder diffraction pattern or the differential scanning calorimetry pattern of a given sample may vary a little (standard deviation) depending on the instrument used, the time and temperature of the sample when measured and standard experimental errors. Therefore, the temperature or the 2-theta values, d-spacing values, heights and relative intensity of the peaks as setforth herein in Tables 1-3 or in FIG. 1-A, 1-B, 2-A, 2-B, 3-A, 3-B, 3-C or 4-A will have an acceptable level of deviation. For example, the values may have an acceptable deviation of e.g., about 20%, 15%, 10%, 5%, 3%, 2% or 1%. In particular embodiment, the 2-theta values or the d-spacing values of the XRPD pattern of the crystals of the current invention may have an acceptable deviation of ±0.2 degrees and/or ±0.2 Å. Further, the XRPD pattern of the Salt Crystals of the invention may be identified by the characteristic peaks as recognized by one skilled in the art. For example, the Salt Crystals of the invention may be identified by e.g., at least five characteristic peaks, e.g., at least three or at least five peaks, e.g., at least three or at least five 2-theta values and/or at least three or at least five d-spacing values as setforth in the XRPD patterns setforth herein. Therefore, the term "corresponding with or substantially as" set forth in any of Tables 1-3 or depicted in any of FIG. 1-A, 2-A, 3-A or 4-A refers to any crystals which has an XRPD having the major or characteristic peaks as set forth in the tables/figures.

The term "about" in front of a numerical value refers to the numerical value itself ±20%, ±15%, ±10%, preferably ±5%, preferably ±3%, preferably ±2%, preferably ±1% of that value. When referencing temperature, the term about refers to the temperature value itself ±10° C., preferably ±5° C., preferably ±3° C. of the reference temperature. In another example, when referencing 2-theta angle values, the term "about" refers to the numerical 2-theta angle value itself ±0.2 degrees of the reference 2-theta angle value. In still another example, when referencing d-spacing values, the term "about" refers to the numerical 2-theta angle value itself ±0.2 Å of the reference d-spacing value.

The Salt Crystals of the invention are selective PDE1 inhibitors. Therefore, the Salt Crystals of the invention are useful for the treatment of PDE1 related disorders as setforth in e.g., WO 2009/075784, WO 2010/132127, WO 2006/133261 and WO 2011/153129, the contents of each of which are incorporated by reference in their entirety.

The term "patient" includes human and non-human. In one embodiment, the patient is a human. In another embodiment, the patient is a non-human.

EXAMPLE 1

Preparation of the Mesylate Salt Crystals

A stock solution of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in methanol (80 mg/ml in MeOH) is prepared. The mixture of 3.301 ml of the stock solution, 0.36 ml water and 22.5 μl (~50 mg) methanesulfonic acid is stirred at room temperature, resulting a clear solution. The mixture/solution is subjected to temperature cycling (40° C./RT, each for 4 h) for overnight (no solid material crashed out). 14 ml Diethyl Ether (anti-solvent) is added, white solid materials is produced gradually and isolated.

X-Ray Powder Diffraction: The XRPD of the mesylate salt crystals is obtained as described or similarly described herein. Approximately 2 mg of the sample is gently compressed on the XRPD zero back ground single obliquely cut silica sample holder. The sample is then loaded into a Philips X-Pert MPD diffractometer and analysed using the following experimental conditions.

Method 1
Tube anode: Cu
Generator tension: 40 kV
Tube current: 40 mA
Wavelength alpha1: 1.5406 A
Wavelength alpha2: 1.5444 A
Start angle [2 theta]: 5.000
End angle [2 theta]: 50.003
Step size: 0.0167113
Time per step: 30.480 seconds
No of step: 2693
Total tine (h:m:s): 00:11:19

For an analysis of XRPD, some material is checked using Method 2 (see below). If S/N (signal to noise ratio) is not good enough then XRPD was repeated using Method 1.

Method 2
Start angle [2 theta]: 5.000
End angle [2 theta]: 49.992
Step size: 0.016
Time per step2.00 seconds
No of step: 2812
Total tine (h:m:s): 00:1:33

The XRPD pattern of the mesylate Salt Crystals is depicted in FIG. 1-A and has peaks as setforth in Table 1 below:

| No. | Pos. [°2Th.] | d-spacing [Å] | Height [cts] | Rel. Int. [%] |
|---|---|---|---|---|
| 1 | 6.2157 | 14.21989 | 62.67 | 10.42 |
| 2 | 8.508 | 10.39309 | 23.98 | 7.97 |
| 3 | 11.5155 | 7.68457 | 166.19 | 27.62 |
| 4 | 12.1461 | 7.28702 | 101.68 | 16.9 |
| 5 | 13.6878 | 6.4695 | 50.11 | 11.1 |
| 6 | 16.5424 | 5.35898 | 127.34 | 24.69 |
| 7 | 16.9484 | 5.23151 | 173.1 | 47.95 |
| 8 | 18.2217 | 4.86872 | 39.94 | 15.49 |
| 9 | 18.8543 | 4.70677 | 601.72 | 100 |
| 10 | 19.2322 | 4.61511 | 190.68 | 36.97 |
| 11 | 19.6408 | 4.52002 | 99.09 | 19.21 |
| 12 | 20.0438 | 4.43004 | 89.5 | 14.87 |
| 13 | 20.622 | 4.30713 | 163.42 | 31.69 |
| 14 | 21.0544 | 4.21963 | 64.38 | 10.7 |
| 15 | 21.2987 | 4.17178 | 233.06 | 45.19 |
| 16 | 21.5693 | 4.12006 | 97.93 | 16.27 |
| 17 | 22.3027 | 3.98621 | 64.13 | 10.66 |
| 18 | 22.9384 | 3.87715 | 203.35 | 33.79 |
| 19 | 23.6005 | 3.76986 | 200.49 | 38.87 |
| 20 | 24.3943 | 3.64896 | 166.22 | 36.83 |
| 21 | 25.1343 | 3.54318 | 63.44 | 10.54 |
| 22 | 25.7457 | 3.4604 | 86.69 | 33.62 |
| 23 | 27.7409 | 3.21589 | 161.76 | 44.8 |
| 24 | 28.1961 | 3.165 | 124.98 | 20.77 |
| 25 | 28.4217 | 3.14039 | 72.04 | 11.97 |
| 26 | 29.3803 | 3.04007 | 61.55 | 13.64 |
| 27 | 29.63 | 3.01502 | 51.92 | 8.63 |
| 28 | 31.2576 | 2.86164 | 57.53 | 15.94 |
| 29 | 31.8561 | 2.80923 | 37.43 | 8.29 |
| 30 | 33.5437 | 2.67166 | 53.93 | 8.96 |
| 31 | 38.3245 | 2.34867 | 14.95 | 9.94 |
| 32 | 39.8831 | 2.2604 | 21.08 | 5.84 |
| 33 | 41.2865 | 2.18675 | 24.75 | 5.48 |
| 34 | 43.5089 | 2.07835 | 27.04 | 14.81 |

Thermogravimetic Analysis (TGA) & Differential Thermal Analysis (DTA) of the mesylate salt crystal of Example 1 is obtained as described or similarly described herein and the DTA is depicted in FIG. 1-B. Approximately 2 mg of sample is weighed into a platinum TGA pan and loaded into a PerkinElmer STA 6000 held at room temperature. The sample is then heated at a rate of 10° C./min to 300° C.

during which time the change in weight is monitored. In addition, DTA is monitored at the same time. The purge gas used is nitrogen at a flow rate of 20 cm3/min. Prior to analysis, the instrument is weight calibrated using a 100 mg reference weight and temperature evaluated using an indium reference standard.

EXAMPLE 2

Preparation of the Fumarate Salt Crystals 180 mg of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one[0.354 mmole] is dissolved in MeOH (2 mL) with heating. Fumaric acid (41 mg) [0.354 mmole] is added to the hot solution. The solution is left at room temperature for 45 minutes for crystallization. The solids are isolated by vacuum filtration. The solids are dried in an oven at 50° C. for 24 hours.

The XRPD of the fumarate salt crystals is obtained as described or similarly described herein. Approximately 20 mg of sample is gently compressed on the XRPD zero back ground single obliquely cut silica sample holder. The sample was then loaded into a Philips X-Pert PRO diffractometer and analysed using the following experimental conditions.

Tube anode: Cu
Generator tension: 40 kV
Tube current: 40 mA
Wavelength alpha1: 1.5406 A
Wavelength alpha2: 1.5444 A
Start angle [2 theta]: 4
End angle [2 theta]: 40
Time per step: 2.5 seconds
Scan step size: 0.016

The XRPD pattern of the fumarate Salt Crystals is depicted in FIG. 2-A and has peaks as setforth in Table 2 below:

| No. | Pos. [°2Th.] | d-spacing [Å] | Height [cts] | Rel. Int. [%] |
|---|---|---|---|---|
| 1 | 5.5976 | 15.78845 | 15.13 | 1.4 |
| 2 | 7.2032 | 12.27251 | 697.12 | 70.13 |
| 3 | 8.0142 | 11.03222 | 583.28 | 36.11 |
| 4 | 10.1187 | 8.742 | 138.56 | 17.16 |
| 5 | 11.1976 | 7.90199 | 218.18 | 30.39 |
| 6 | 11.7461 | 7.53423 | 525.96 | 81.4 |
| 7 | 12.5036 | 7.07943 | 168.07 | 15.61 |
| 8 | 13.2367 | 6.68895 | 407.76 | 34.71 |
| 9 | 14.1892 | 6.24199 | 232.02 | 10.77 |
| 10 | 14.4233 | 6.1412 | 329.19 | 20.38 |
| 11 | 14.7399 | 6.01002 | 188.07 | 11.64 |
| 12 | 15.5157 | 5.71122 | 639.38 | 29.69 |
| 13 | 16.0172 | 5.53349 | 316.16 | 34.25 |
| 14 | 16.6971 | 5.30968 | 158.43 | 19.62 |
| 15 | 17.322 | 5.11951 | 442.23 | 20.53 |
| 16 | 19.7866 | 4.48704 | 203.55 | 18.9 |
| 17 | 20.3297 | 4.36838 | 555.19 | 51.56 |
| 18 | 21.1031 | 4.21 | 689.14 | 95.99 |
| 19 | 21.9181 | 4.05526 | 1199.87 | 83.57 |
| 20 | 22.9016 | 3.8833 | 375.79 | 34.9 |
| 21 | 23.6407 | 3.76354 | 577.36 | 62.55 |
| 22 | 24.4164 | 3.64569 | 872.48 | 54.01 |
| 23 | 24.9125 | 3.57422 | 422.71 | 52.34 |
| 24 | 26.1016 | 3.41403 | 212.31 | 23 |
| 25 | 26.6168 | 3.3491 | 527.74 | 89.85 |
| 26 | 27.3903 | 3.25625 | 278.33 | 21.54 |
| 27 | 27.8762 | 3.20059 | 646.12 | 100 |
| 28 | 29.0497 | 3.07391 | 179.56 | 16.67 |
| 29 | 29.8276 | 2.9955 | 349.25 | 27.03 |
| 30 | 30.6371 | 2.91817 | 187.24 | 14.49 |
| 31 | 31.7612 | 2.81741 | 173.36 | 16.1 |
| 32 | 32.5634 | 2.74981 | 155.03 | 19.2 |
| 33 | 33.5077 | 2.67444 | 161.64 | 15.01 |
| 34 | 35.0864 | 2.55764 | 222.69 | 24.13 |
| 35 | 36.3098 | 2.47422 | 149.42 | 23.13 |
| 36 | 38.2838 | 2.34912 | 154.74 | 47.37 |
| 37 | 38.9662 | 2.31528 | 116.83 | 23.84 |

Differential Scanning Calorimetry (DSC) thermograph of the fumarate Salt Crystals is obtained as described or similarly described herein and the DSC is depicted in FIG. 2-B. Approximately 4 mg of sample is weighed into an aluminium DSC pan and sealed using a hermetic lid (crimped). The sample is then loaded into a Perkin-Elmer DSC7 at 0° C. The sample is heated from 25° C. to around 250° C. at scan rate of one of 10° C./min and the resulting heat flow response is monitored. A 20 cm³/min nitrogen purge is used to prevent thermally induced oxidation of the sample during heating and to reduce the thermal lag through the sample to increase the instrument sensitivity. Prior to analysis, the instrument is temperature and heat-flow calibrated using an indium reference standard.

EXAMPLE 3

Preparation of the Mono-Phosphate Salt Crystals

The mono-phosphate salt crystals of the invention may be prepared as described or similarly described herein. A 3 L three-neck round bottom flask in a heating mantle with a mechanical stirrer, thermocouple, nitrogen inlet, addition funnel, reflux condenser and a drying tube is prepared. (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base (147 g, SM) and acetonitrile (1470 mL, 10 mL/g SM) is charged to the flask and stirred. The resulting solution is heated to 40-45° C. A solution of 85 wt. % phosphoric acid (33.4 g, 0.227 g/g SM) in acetonitrile (265 mL, 1.8 mL/g SM) is slowly added over a minimum of 1 hour, maintaining the reaction mixture at 40-45° C. The addition funnel is rinsed with acetonitrile (29 mL, 0.2 mL/g SM). Heating is removed and the reaction mixture is stirred under nitrogen at ambient temperature over 12-24 hours. The solids are filtered and rinsed with acetonitrile (2×294 mL; 2×2 mL/g SM). The product is dried in a vacuum oven at 70-75° C. with nitrogen bleed over a minimum of 12 hours to yield a constant weight.

The XRPD of the mono-phosphate salt crystals is obtained as described or similarly described herein. The result is depicted in FIG. 3-A. Approximately 20 mg of sample is gently compressed on the XRPD zero back ground single obliquely cut silica sample holder. The sample is then loaded into a Philips X-Pert PRO diffractometer and analysed using the following experimental conditions.

Tube anode: Cu
Generator tension: 40 kV
Tube current: 40 mA
Wavelength alpha1: 1.5406 A
Wavelength alpha2: 1.5444 A
Start angle [2 theta]: 4
End angle [2 theta]: 40
Time per step: 2.5 seconds
Scan step size: 0.016

The XRPD pattern of the mono-phosphate Salt Crystals is depicted in FIG. 3-A and has peaks as setforth in Table 3 below:

| No. | Pos. [°2Th.] | d-spacing [Å] | Height [cts] | Rel. Int. [%] |
|---|---|---|---|---|
| 1 | 5.7553 | 15.35618 | 1887.34 | 73.85 |
| 2 | 6.8867 | 12.8358 | 176.68 | 10.75 |
| 3 | 7.5188 | 11.75808 | 53.19 | 2.78 |
| 4 | 9.4821 | 9.32747 | 328.23 | 22.83 |
| 5 | 10.9511 | 8.07934 | 133.75 | 4.65 |
| 6 | 11.7509 | 7.53118 | 226.95 | 7.89 |
| 7 | 11.8625 | 7.46054 | 201.05 | 5.24 |
| 8 | 12.7859 | 6.92377 | 149.08 | 6.48 |
| 9 | 13.7504 | 6.44022 | 456.19 | 15.87 |
| 10 | 13.9906 | 6.33014 | 633 | 44.04 |
| 11 | 15.3855 | 5.75923 | 245.11 | 12.79 |
| 12 | 16.2789 | 5.44515 | 1277.75 | 100 |
| 13 | 17.2688 | 5.13515 | 241.96 | 10.52 |
| 14 | 17.6964 | 5.01205 | 312.05 | 18.99 |
| 15 | 18.5004 | 4.796 | 690.64 | 36.03 |
| 16 | 18.8841 | 4.6994 | 800.41 | 27.84 |
| 17 | 19.2158 | 4.61904 | 859.15 | 74.71 |
| 18 | 20.6821 | 4.29474 | 559.5 | 14.6 |
| 19 | 22.2013 | 4.00417 | 641.59 | 50.21 |
| 20 | 22.8385 | 3.89388 | 682.56 | 41.55 |
| 21 | 23.2185 | 3.83102 | 555.61 | 24.16 |
| 22 | 23.8425 | 3.73215 | 697.52 | 54.59 |
| 23 | 24.4086 | 3.64685 | 357.59 | 18.66 |
| 24 | 25.8905 | 3.44137 | 842.43 | 29.3 |
| 25 | 27.9329 | 3.19423 | 221.79 | 11.57 |
| 26 | 29.6611 | 3.01192 | 250.43 | 26.13 |
| 27 | 31.3753 | 2.85118 | 306.23 | 15.98 |
| 28 | 32.863 | 2.72542 | 167.88 | 20.44 |
| 29 | 34.6203 | 2.591 | 111.05 | 7.73 |
| 30 | 36.2262 | 2.47975 | 92.41 | 4.82 |
| 31 | 37.5261 | 2.39678 | 105.94 | 6.45 |
| 32 | 41.1361 | 2.19441 | 25.77 | 4.03 |
| 33 | 45.786 | 1.98015 | 21.45 | 4.92 |

Thermogravimetic Analysis (TGA) & Differential Thermal Analysis (DTA) of the mono-phosphate salt crystals is obtained as described or similarly described herein and the DTA is depicted in FIG. 3-B. Approximately 5 mg of sample is weighed accurately into a ceramic crucible and it is placed into the chamber of Perkin-Elmer STA 600 TGA/DTA analyzer at ambient temperature. The sample is heated at a rate of 10° C./min from 25° C. to 300° C. during which time the change in weight is monitored as well as the DTA signal. The purge gas used is nitrogen at a flow rate of 20 cm$^3$/min. Prior to analysis the instrument is weight calibrated using a 100 mg reference weight and temperature calibrated using an indium reference standard.

Differential Scanning Calorimetry (DSC) thermograph of the mono-phosphate Salt Crystals is obtained as described or similarly described herein and the DSC is depicted in FIG. 3-C. Approximately 4 mg of sample is weighed into an aluminium DSC pan and sealed using a hermetic lid (crimped). The sample is then loaded into a Perkin-Elmer DSC7 at 0° C. The sample is heated from 25° C. to around 250° C. at scan rate of one of 10° C./min and the resulting heat flow response is monitored. A 20 cm$^3$/min nitrogen purge is used to prevent thermally induced oxidation of the sample during heating and to reduce the thermal lag through the sample to increase the instrument sensitivity. Prior to analysis, the instrument is temperature and heat-flow calibrated using an indium reference standard.

The mono-phosphate Salt Crystals are particularly stable, has good solubility, low hygroscopicity, high melting point, has plate-like morphology and are non-solvate, none-hydrate, all of which are desirable properties for galenic formulation.

Alternative to the process described above, the mono-phosphate salt crystals may also be prepared by dissolving the (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base in non-solvate or solvate (e.g., mono-ethanol, methanol, n-propanol, isopropanol, n-butanol solvate or non-solvate) crystal form in a suitable solvent (e.g., in acetonitrile at 50° C. or in acetone at 38° C.). Active charcoal is added and the mixture is stirred at the same temperature for 0.5 h. After removing the active charcoal by filtration, the fitrate is warmed to 50° C. (if acetonitrile is used) or 32-39° C. (if acetone is used). An equimolar amount of 85 wt. % phosphoric acid in a suitable solvent (e.g., acetonitrile or acetone) is added. After addition of water, the mixture is stirred at 20-70° C., e.g., 50° C. or 40° C. The mono-phosphate crystals are then isolated by filtration.

The free base crystals may be prepared by (1) stirring (6aR,9aS)-3-chloro-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one in a suitable solvent (e.g., combination of DMAc and xylene) in the presence of base (e.g. potassium carbonate), aniline, palladium catalyst (e.g., Pd(OAc)$_2$) and ligand (e.g., xantphos), then separating organic layer; (2) adding the solvent corresponding to objective solvate form (e.g., adding ethanol to form an ethanol solvate) to the organic layer obtained in the step 1). n-Heptane may be added at 70° C. and then cooled to 5° C. and stirred. The crystals may be separated by filtration. Preferably, step (1) is carried out under nitrogen atmosphere and the separated organic layer is washed with a suitable solution (DMAc or xylene) and then treated with charcoal to remove residual palladium catalyst. The free base crystal may also be prepared by using seed crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in non-solvate form.

The method of making the Compound (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one is generally described in WO 2009/075784, the contents of which are incorporated by reference in their entirety. This compound can also be prepared as summarized or similarly summarized in the following reaction scheme.

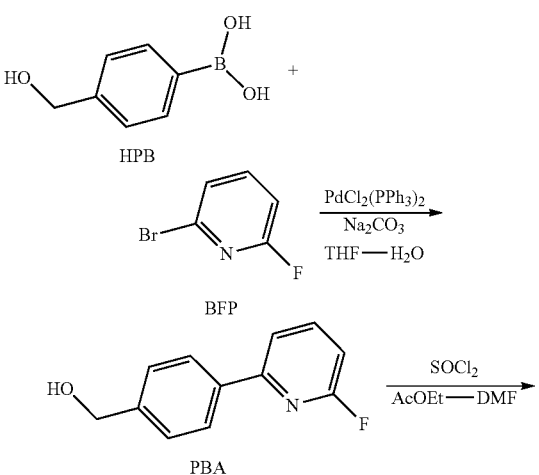

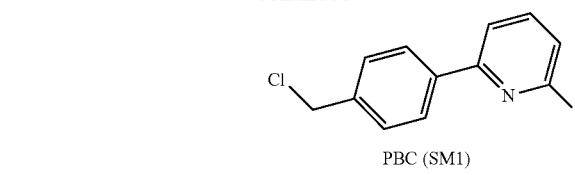
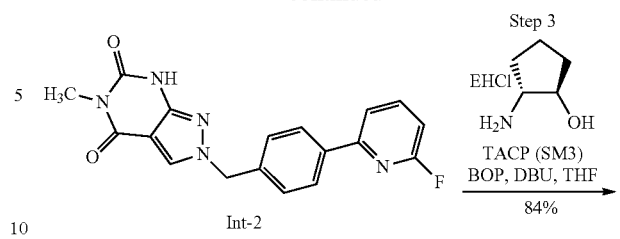
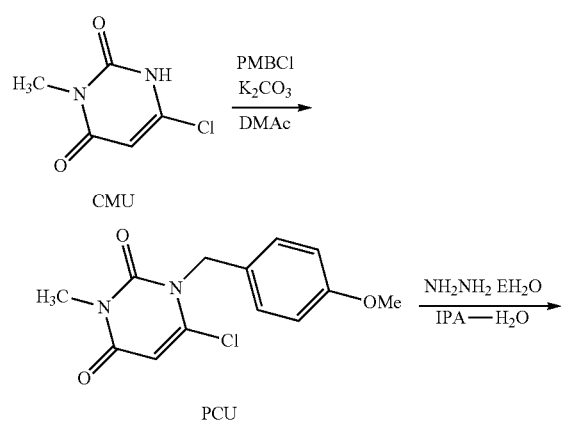
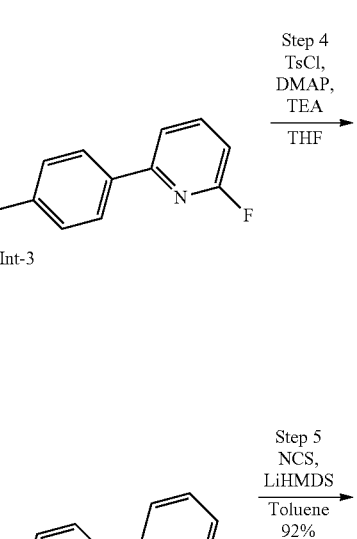
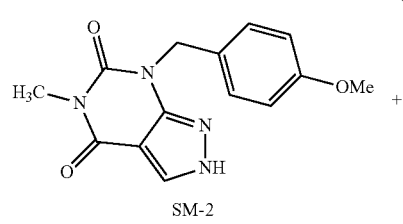
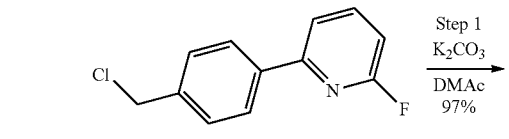
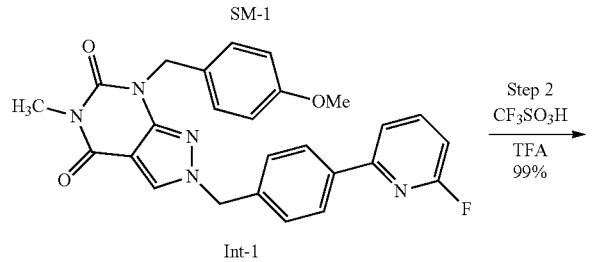

-continued

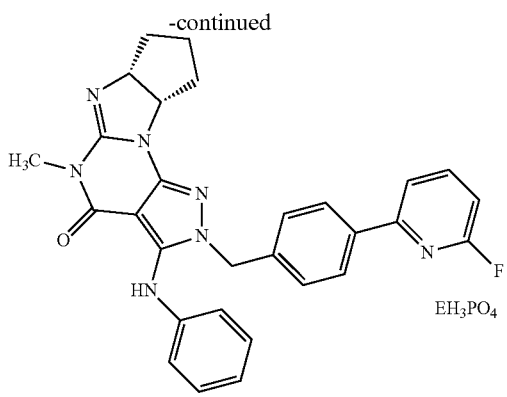

In particular, (6aR,9aS)-3-chloro-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one may be prepared as described or similarly described below.

Preparation of (6aR,9aS)-3-chloro-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one (4-(6-fluoropyridin-2-yl)phenyl)methanol

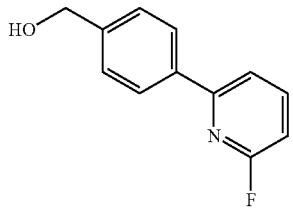 [SMILES: OCc1ccc(-c2cccc(F)n2)cc1]

The mixture of Na$_2$CO$_3$ (121 g), water (500 mL), THF (650 mL), PdCl$_2$(PPh$_3$)$_2$ (997 mg), 2-bromo-6-fluoropyridine (100 g) and 4-(hydroxymethyl)phenylboronic acid (90.7 g) is stirred at 65° C. for 4 h under the nitrogen atmosphere. After cooling to room temperature, THF (200 mL) is added. The organic layer is separated and washed with 5% NaCl solution twice. The organic layer is concentrated to 400 mL. After the addition of toluene (100 mL), heptane (500 mL) is added at 55° C. The mixture is cooled to room temperature. The crystals are isolated by filtration, washed with the mixture of toluene (100 mL) and heptane (100 mL) and dried to give (4-(6-fluoropyridin-2-yl)phenyl)methanol (103 g). $^1$H NMR (500 MHz, CDCl$_3$) δ 1.71-1.78 (m, 1H), 4.74-4.79 (m, 2H), 6.84-6.88 (m, 1H), 7.44-7.50 (m, 2H), 7.61-7.65 (m, 1H), 7.80-7.88 (m, 1H), 7.98-8.04 (m, 2H).

2-(4-(chloromethyl)phenyl)-6-fluoropyridine

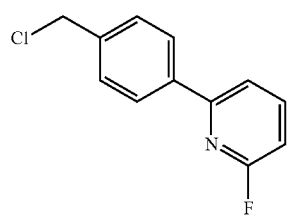 [SMILES: Fc1cccc(-c2ccc(CCl)cc2)n1]

The solution of thionylchloride (43.1 mL) in AcOEt (200 mL) is added to the mixture of (4-(6-fluoropyridin-2-yl)phenyl)methanol (100 g), DMF (10 mL) and AcOEt (600 mL) at room temperature. The mixture is stirred at room temperature for 1 h. After cooling to 10° C., 15% Na$_2$CO$_3$ solution is added. The organic layer is separated and washed with water (500 mL) and 5% NaCl solution (500 mL) twice. The organic layer is concentrated to 500 mL. After the addition of EtOH (500 mL), the mixture is concentrated to 500 mL. After addition of EtOH (500 mL), the mixture is concentrated to 500 mL. After the addition of EtOH (500 mL), the mixture is concentrated to 500 mL. After addition of EtOH (200 mL), water (700 mL) is added at 40° C. The mixture is stirred at room temperature. The crystals are isolated by filtration and dried to give 2-(4-(chloromethyl)phenyl)-6-fluoropyridine (89.5 g). $^1$H NMR (500 MHz, CDCl$_3$) δ 4.64 (s, 2H), 6.86-6.90 (m, 1H), 7.47-7.52 (m, 2H), 7.60-7.65 (m, 1H), 7.82-7.88 (m, 1H), 7.98-8.03 (m, 2H).

6-chloro-1-(4-methoxybenzyl)-3-methylpyrimidine-2,4(1H,3H)-dione

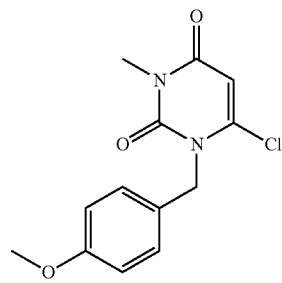 [SMILES: COc1ccc(Cn2c(Cl)cc(=O)n(C)c2=O)cc1]

The mixture of 6-chloro-3-methyluracil (100 g), p-methoxybenzylchloride (107 g), K$_2$CO$_3$ (86.1 g) and DMAc (600 mL) is stirred at 75° C. for 4 h. Water (400 mL) is added at 45° C. and the mixture is cooled to room temperature. Water (800 mL) is added and the mixture is stirred at room temperature. The crystals are isolated by filtration, washed with the mixture of DMAc and water (1:2, 200 mL) and dried to give 6-chloro-1-(4-methoxybenzyl)-3-methylpyrimidine-2,4(1H,3H)-dione (167 g). $^1$H NMR (500 MHz, CDCl$_3$) δ 3.35 (s, 3H), 3.80 (s, 3H), 5.21 (s, 2H), 5.93 (s, 1H), 6.85-6.89 (m, 2H), 7.26-7.32 (m, 2H).

6-hydrazinyl-1-(4-methoxybenzyl)-3-methylpyrimidine-2,4(1H,3H)-dione

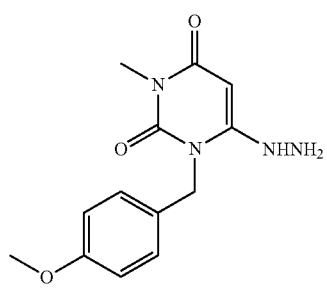 [SMILES: COc1ccc(Cn2c(NN)cc(=O)n(C)c2=O)cc1]

The mixture of 6-chloro-1-(4-methoxybenzyl)-3-methyl-pyrimidine-2,4(1H,3H)-dione (165 g), IPA (990 mL), water (124 mL) and hydrazine hydrate (62.9 mL) is stirred at room temperature for 1 h. The mixture is warmed to 60° C. and stirred at the same temperature for 4 h. Isopropyl acetate (1485 mL) is added at 45° C. and the mixture is stirred at the same temperature for 0.5 h. The mixture is cooled at 10° C. and stirred for 1 h. The crystals are isolated by filtration, washed with the mixture of IPA and isopropyl acetate (1:2, 330 mL) and dried to give 6-hydrazinyl-1-(4-methoxybenzyl)-3-methylpyrimidine-2,4(1H,3H)-dione (153 g). $^1$H NMR (500 MHz, DMSO-d$_6$) δ 3.12 (s, 3H), 3.71 (s, 3H), 4.36 (s, 2H), 5.01 (s, 2H), 5.14 (s, 1H), 6.87-6.89 (m, 2H), 7.12-7.17 (m, 2H), 8.04 (s, 1H).

7-(4-methoxybenzyl)-5-methyl-2H-pyrazolo[3,4-d]pyrimidine-4,6(5H,7H)-dione

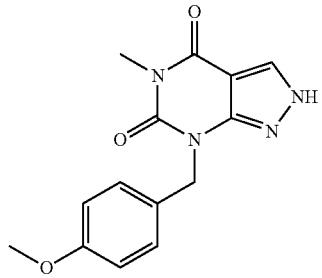 [SMILES: COc1ccc(Cn2c(=O)n(C)c(=O)c3c[nH]nc32)cc1]

To the mixture of DMF (725 mL) and 6-hydrazinyl-1-(4-methoxybenzyl)-3-methylpyrimidine-2,4(1H,3H)-dione (145 g) is added POCl$_3$ (58.5 mL) at 5° C. The mixture is stirred at room temperature for 1 h. Water (725 mL) is added at 50° C. and the mixture is stirred at room temperature for 1 h. The crystals are isolated by filtration, washed with the mixture of DMF and water (1:1, 290 mL) and dried to give 7-(4-methoxybenzyl)-5-methyl-2H-pyrazolo[3,4-d]pyrimidine-4,6(5H,7H)-dione (145 g). $^1$H NMR (500 MHz, DMSO-d$_6$) δ 3.23 (s, 3H), 3.71 (s, 3H), 5.05 (s, 2H), 6.82-6.90 (m, 2H), 7.28-7.36 (m, 2H), 8.48 (s, 1H), 13.51 (br, 1H).

2-(4-(6-fluoropyridin-2-yl)benzyl)-7-(4-methoxybenzyl)-5-methyl-2H-pyrazolo[3,4-d]pyrimidine-4,6(5H,7H)-dione

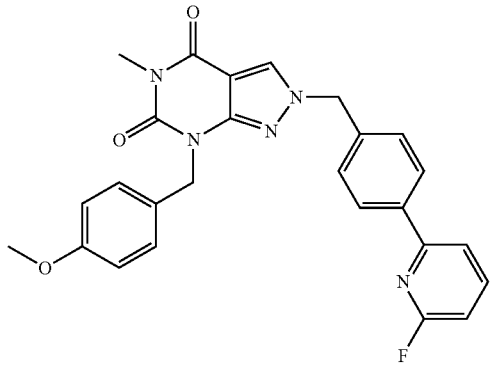 [SMILES: COc1ccc(Cn2c(=O)n(C)c(=O)c3cn(Cc4ccc(-c5cccc(F)n5)cc4)nc32)cc1]

The mixture of 2-(4-(chloromethyl)phenyl)-6-fluoropyridine (100 g), 7-(4-methoxybenzyl)-5-methyl-2H-pyrazolo[3,4-d]pyrimidine-4,6(5H,7H)-dione (129 g), K$_2$CO$_3$ (62.3 g) and DMAc (1500 mL) is stirred at 45° C. for 5 h. Water (1500 mL) is added at 40° C. and the mixture is stirred at room temperature for 1 h. The crystals are isolated by filtration, washed with the mixture of DMAc and water (1:1, 500 mL) and dried to give 2-(4-(6-fluoropyridin-2-yl)benzyl)-7-(4-methoxybenzyl)-5-methyl-2H-pyrazolo[3,4-d]pyrimidine-4,6(5H,7H)-dione (207 g). $^1$H NMR (500 MHz, DMSO-d$_6$) δ 3.21 (s, 3H), 3.66 (s, 3H), 4.98 (s, 2H), 5.45 (s, 2H), 6.77-6.82 (m, 2H), 7.13-7.16 (m, 1H), 7.25-7.30 (m, 2H), 7.41-7.44 (m, 2H), 7.92-7.96 (m, 1H), 8.04-8.11 (m, 3H), 8.68 (s, 1H).

2-(4-(6-fluoropyridin-2-yl)benzyl)-5-methyl-2H-pyrazolo[3,4-d]pyrimidine-4,6(5H,7H)-dione

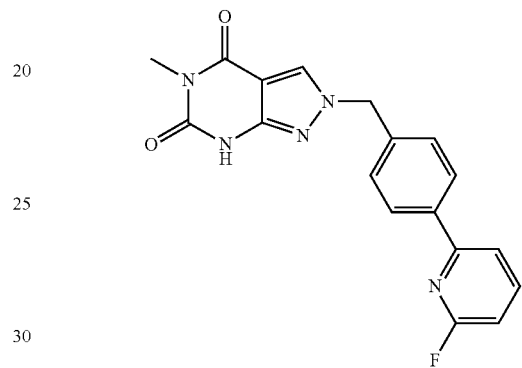

The mixture of 2-(4-(6-fluoropyridin-2-yl)benzyl)-7-(4-methoxybenzyl)-5-methyl-2H-pyrazolo[3,4-d]pyrimidine-4,6(5H,7H)-dione (105 g), CF$_3$COOH (300 mL) and CF$_3$SO$_3$H (100 g) is stirred at room temperature for 10 h. Acetonitrile (1000 mL) is added. The mixture is added to the mixture of 25% NH$_3$ (1000 mL) and acetonitrile (500 mL) at 10° C. The mixture is stirred at room temperature for 1 h. The crystals are isolated by filtration, washed with the mixture of acetonitrile and water (1:1, 500 mL) and dried to give the crude product. The mixture of the crude product and AcOEt (1200 mL) is stirred at room temperature for 1 h. The crystals are isolated by filtration, washed with AcOEt (250 mL) and dried to give 2-(4-(6-fluoropyridin-2-yl)benzyl)-5-methyl-2H-pyrazolo[3,4-d]pyrimidine-4,6(5H,7H)-dione (75.3 g). $^1$H NMR (500 MHz, DMSO-d$_6$) δ 3.16 (s, 3H), 3.50-4.00 (br, 1H), 5.40 (s, 2H), 7.13-7.16 (m, 1H), 7.41-7.44 (m, 2H), 7.91-7.94 (m, 1H), 8.04-8.10 (m, 3H), 8.60 (s, 1H).

2-(4-(6-fluoropyridin-2-yl)benzyl)-6-(((1R,2R)-2-hydroxycyclopentyl)amino)-5-methyl-2H-pyrazolo[3,4-d]pyrimidin-4(5H)-one

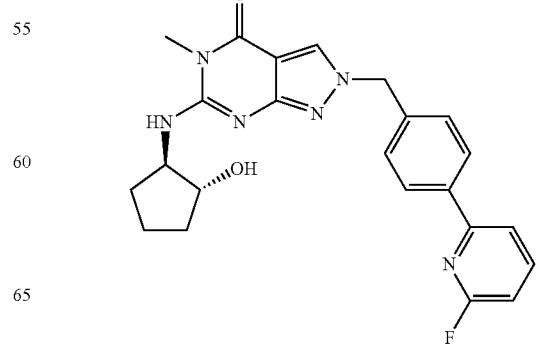

The mixture of BOP reagent (126 g), 2-(4-(6-fluoropyridin-2-yl)benzyl)-5-methyl-2H-pyrazolo[3,4-d]pyrimidine-4,6(5H,7H)-dione (80 g), DBU (136 mL) and THF (1120 mL) is stirred at room temperature for 1 h. (1R,2R)-2-Aminocyclopentanol hydrochloride (37.6 g) and THF (80 mL) are added and the mixture is stirred at room temperature for 5 h. After the addition of 5% NaCl (400 mL) and AcOEt (800 mL), the organic layer is separated. The organic layer is washed with 10% NaCl (400 mL), 1M HCl 15% NaCl (400 mL), 5% NaCl (400 mL), 5% NaHCO₃ (400 mL) and 5% NaCl (400 mL) successively. After treatment with active charcoal, the organic layer is concentrated to 400 mL. After the addition of acetonitrile (800 mL), the mixture is concentrated to 400 mL. After the addition of acetonitrile (800 mL), seed crystals are added at 40° C. The mixture is concentrated to 400 mL. Water (800 mL) is added at room temperature and the mixture is stirred for 2 h. The crystals are isolated by filtration, washed with the mixture of acetonitrile and water (1:2, 400 mL) and dried to give 2-(4-(6-fluoropyridin-2-yl)benzyl)-6-(((1R,2R)-2-hydroxycyclopentyl)amino)-5-methyl-2H-pyrazolo[3,4-d]pyrimidin-4(5H)-one (81.7 g). ¹H NMR (500 MHz, CDCl₃) δ 1.47-1.59 (m, 1H), 1.68-1.93 (m, 3H), 2.02-2.12 (m, 1H), 2.24-2.34 (m, 1H), 3.42 (s, 3H), 3.98-4.12 (m, 2H), 4.68-4.70 (m, 1H), 5.37 (s, 2H), 6.86-6.90 (m, 1H), 7.36-7.42 (m, 2H), 7.58-7.63 (m, 1H), 7.81-7.88 (m, 1H), 7.89 (s, 1H), 7.97-8.01 (m, 2H).

(6aR,9aS)-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one

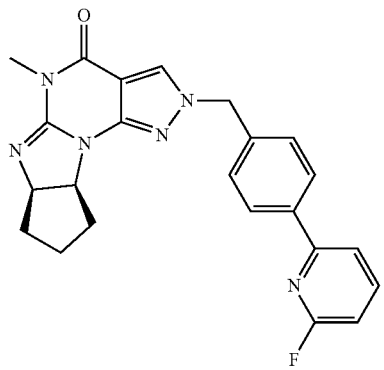 [SMILES: CN1C(=O)c2cn(Cc3ccc(-c4cccc(F)n4)cc3)nc2N2C1=N[C@@H]1CCC[C@@H]12]

The mixture of 2-(4-(6-fluoropyridin-2-yl)benzyl)-6-(((1R,2R)-2-hydroxycyclopentyl)amino)-5-methyl-2H-pyrazolo[3,4-d]pyrimidin-4(5H)-one (80 g), p-toluenesulfonylchloride (38.6 g), Et₃N (28.2 mL), N,N-dimethylaminopyridine (24.7 g) and THF (800 mL) is stirred at 50° C. for 10 h. To the mixture is added 8M NaOH (11.5 mL) at room temperature and the mixture is stirred for 2 h. After the addition of 5% NaCl (400 mL) and AcOEt (800 mL), the organic layer is separated. The organic layer is washed with 5% NaCl (400 mL) twice. The organic layer is concentrated to 240 mL. After the addition of MeOH (800 mL), the mixture is concentrated to 240 mL. After the addition of MeOH (800 mL), the mixture is concentrated to 240 mL. After the addition of MeOH (160 mL), the mixture is stirred at room temperature for 1 h and at 0° C. for 1 h. The crystals are isolated by filtration, washed with cold MeOH (160 mL) and dried to give (6aR,9aS)-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one (55.7 g). ¹H NMR (500 MHz, CDCl₃) δ 1.39-1.54 (m, 1H), 1.58-1.81 (m, 3H), 1.81-1.92 (m, 1H), 2.12-2.22 (m, 1H), 3.28 (s, 3H), 4.61-4.70 (m, 2H), 5.20 (s, 2H), 6.79-6.85 (m, 1H), 7.25-7.32 (m, 2H), 7.53-7.58 (m, 1H), 7.68 (s, 1H), 7.75-7.83 (m, 1H), 7.92-7.98 (m, 2H).

(6aR,9aS)-3-chloro-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one

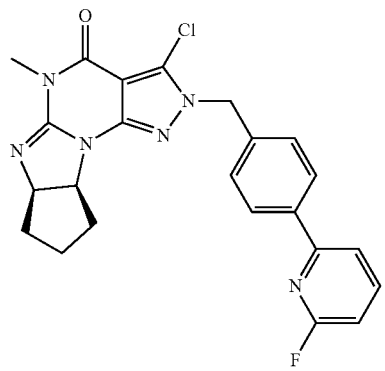 [SMILES: CN1C(=O)c2c(nn(Cc3ccc(-c4cccc(F)n4)cc3)c2Cl)N2C1=N[C@@H]1CCC[C@@H]12]

The mixture of (6aR,9aS)-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one (50 g) and toluene (1000 mL) is concentrated to 750 mL under the nitrogen atmosphere. Toluene (250 mL) and NCS (24 g) is added. To the mixture is added LiHMDS (1M THF solution, 204 mL) at 0° C. and the mixture is stirred for 0.5 h. To the mixture is added 20% NH₄Cl (50 mL) at 5° C. The mixture is concentrated to 250 mL. After the addition of EtOH (250 mL), the mixture is concentrated to 150 mL. After the addition of EtOH (250 mL), the mixture is concentrated to 200 mL. After the addition of EtOH (200 mL), the mixture is warmed to 50° C. Water (300 mL) is added and the mixture is stirred at 50° C. for 0.5 h. After stirring at room temperature for 1 h, the crystals are isolated by filtration, washed with the mixture of EtOH and water (1:1, 150 mL) and dried to give (6aR,9aS)-3-chloro-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one (51.1 g). ¹H NMR (500 MHz, CDCl₃) δ 1.46-1.61 (m, 1H), 1.67-1.90 (m, 3H), 1.92-2.00 (m, 1H), 2.19-2.27 (m, 1H), 3.37 (s, 3H), 4.66-4.77 (m, 2H), 5.34 (s, 2H), 6.87-6.93 (m, 1H), 7.35-7.41 (m, 2H), 7.59-7.65 (m, 1H), 7.82-7.91 (m, 1H), 7.97-8.05 (m, 2H).

EXAMPLE 4

Preparation of the L-Tartrate Salt Crystals 60 mg of the (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base [0.118 mmole] is dissolved in Acetone (3 mL). L-tartaric acid (17.7 mg) [0.118 mmole] is added to the solution. The solution is left at room temperature for 30 minutes for crystallization. The solids are isolated by vacuum filtration, then the solids are air dried for 20 minutes. The XRPD of the L-tartrate salt crystals is obtained as described or similarly described in Example 2. The result is depicted in FIG. 4-A.

EXAMPLE 5

Solubility Study of Phosphate Salt Crystals

The (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one mono-phosphate salt crystals are assessed for its aqueous solubility at lower pH. The (amorphous) free base is also tested for reference at a limited range of pH.

Phosphate (buffer) solutions are made at 50 mM concentration and the pH is adjusted to pH 2, 3, 4, 5 or 6.8 using either 3M phosphoric acid (lower pH) or 3M NaOH (higher pH). 0.1N HCl is also used, pH is measured as 1.2.

20 mg of the (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one mono-phosphate salt crystals or free base is weighed into a glass vial, and 2 ml of the relevant aqueous media is added. The vials are shaken. After 1 hr, a sample (~1 ml) is removed via syringe, and filtered through a syringe filter (0.2 micron) into an HPLC vial. After shaking the suspensions for 16 hours, a second sample is taken. All samples are then diluted with the HPLC diluent by a factor of 1000 (except the pH 6.8 samples which are diluted ×10), and re-analysed by HPLC. In cases where the entire solid dissolved, the 2 ml solution is added to another 20 mg salt or free base.

The solubility study shows that the mono-phosphate salt crystals have similar solubility to the amorphous free base at low pH (pH 1.2 and 2) in the range of 16->20 mg/ml. The mono-phosphate salt crystals show better solubility than the amorphous free base at pH 3 and gives solubility of up to 7.7 mg/ml at pH 4. The results are summarized below:

| pH | Solubility after 1 hr (mg/ml) | Solubility after 16 hrs (mg/ml) |
|---|---|---|
| Phosphate salt | | |
| 1.2 | >20 | >20 |
| 2 | 13.6 | 17.0 |
| 3 | 8.4 | 9.4 |
| 4 | 2.5 | 7.7 |
| 5 | Below detection limit* | Below detection limit* |
| 6.8 | Below detection limit* | Below detection limit* |
| Free base API (amorphous) | | |
| 1.2 | >20 | >20 |
| 2 | >20 | >20 |
| 3 | 2.5 | 2.2 |

*after dilution. Samples at pH 5 are diluted 1000 times before HPLC analysis; and samples at pH 6.8 are diluted 10 times.

EXAMPLE 6

USP2 Dissolution Study at pH 1 and 4.5

The rate of dissolution is an important factor in the bioavailability of an active pharmaceutical ingredient (API). This is commonly tested using standard conditions e.g. USP 2 dissolution testing. The pH of the aqueous media used can be correlated with the pH of the stomach (low pH ~1-2) and the intestines (intermediate acidic pH ~4-6). Therefore pH 1 (0.1 M HCl) and a citrate buffer at pH 4.5 (0.2M) are used for the dissolution testing.

The (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one mono-phosphate salt crystals are weighed (×4) into size 0 white gelatine capsules at 119 mg per capsule (equivalent to 100 mg API). The (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo-[1,2-a]pyrazolo[4,3-e]pyrimidin-4(2H)-one is also weighed (×2) into white gelatine capsules at 100 mg per capsule. These capsules are then dissolved using the standard set up of the USP 2 dissolution equipment i.e., in 1000 mL of the relevant aqueous media, stirrers set at 50 rpm, capsules placed in metal coils to weigh them down, media equilibrated with the water bath set at 37"C. Analytical samples are removed via canula, with an initial filter on the canula and secondary filtering through 0.2 micron syringe filters. The samples are then analysed without dilution by HPLC for API content. Calibration for HPLC is run using both the free base API and the phosphate salt.

This study shows that the mono-phosphate salt crystals and the amorphous free base at low pH (pH 1) have good solubility. At about 0.1 mg/mL (API equivalent), full dissolution is observed after approximately 15 minutes. Both the mono-phosphate salt crystals dissolution study show better dissolution rates than the free base. The dissolution profiles of the mono-phosphate salt crystals and the free base at pH 1 are depicted in FIG. 5-A. The dissolution profiles of the mono-phosphate salt crystals and the free base at pH 4.5 are depicted in FIG. 5-B.

EXAMPLE 7

Bridging Study of Monophosphate Salt and Free Base in Dog

The mono-phosphate salt of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one is administered to dogs at a dose of 40 mg/kg in gelatin capsules or via oral gavage in a vehicle formulation of HCl-Citrate, pH 3.5, 0.5% methylcellulose in water. These data are compared to another study of the free base study in which the (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base is administered via oral gavage to dogs at 40 mg/kg in a vehicle containing HCl-Citrate, pH 3.5, 0.5% methylcellulose in water. The analysis of drug concentration in plasma samples collected is analyzed.

The pharmacokinetic (PK) parameters are determined from the plasma concentration versus time data by non-compartmental methods with uniform weighting (PK solutions 2.0™, Summit Research Services, Montrose, Colo.). The maximum observed concentration (Cmax) and the time of the maximum observed concentration (tmax) are obtained from the bioanalytical raw data. The area-under-the-plasma concentration-time curve from time zero to the time of the last measurable sample (AUC_) is calculated by the trapezoidal rule. The plasma pharmacokinetic (PK) profile of the free base and the phosphate salt crystal in 40 mg/kg dosage is provided in Tables 5 and 6 below.

TABLE 5

| | Route | | | | | | | | |
|---|---|---|---|---|---|---|---|---|---|
| | Oral Gavage Phosphate Salt | | | | | Oral Capsule Phosphare Salt | | | |
| Dog Number | M-1001 | M-1002 | F-1101 | F-1102 | Mean | M-2001 | M-2002 | F-2102 | Mean |
| E Half-life (hr) | 7.8 | 12.0 | 6.6 | 5.5 | 8.7 | 4.6 | 7.8 | 6.2 | 7.3 |
| Cmax (obs) (ng/mL) | 918 | 1519 | 1083 | 1356 | 1158 | 2431 | 1529 | 1470 | 1331 |
| Tmax (obs) (hr) | 8 | 4 | 4 | 8 | 4 | 2 | 2 | 8 | 2 |
| AUC¥ (area) (ng-hr/mL) | 16864 | 31593 | 16208 | 21323 | 21300 | 13161 | 21861 | 20547 | 18742 |

TABLE 6

| | Route Oral Gavage Free Base Dog Number | | | | |
|---|---|---|---|---|---|
| | M-5001 | M-5002 | F-5101 | F-5102 | Mean |
| E Half-life (hr) | 14.8 | 16.7 | 6.7 | 5.5 | 10.8 |
| Cmax (obs) (ng/mL) | 902 | 1315 | 674 | 2005 | 1021 |
| Tmax (obs) (hr) | 4 | 4 | 8 | 2 | 4 |
| AUC¥ (area) (ng-hr/mL) | 20070 | 36454 | 11548 | 14256 | 19199 |

EXAMPLE 8

Single Rising Dose Clinical Study

In a single rising dose clinical study involving 55 active subjects (15 placebo) with 11 active:3 placebo for each dose level of 10, 25, 75, 150, 300 mg, the mono-phosphate salt crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one is dissolved in water, and this aqueous solution is orally administered. The pharmacokinetic profile is setforth below in Table 7.

TABLE 7

| Dose (mg) | Weight Mean [kg]) | Mono-Phosphate Salt | Tmax (hr) | Cmax (ng/mL) | AUC(0-tlqc) (ng · hr/mL) | AUC(0-inf) (ng · hr/mL) |
|---|---|---|---|---|---|---|
| 10 | 75.8 | Mean (SD) | 1.00 (0.50-1.50) | 89.66 (15.486) | 767.50 (230.433) | 771.80 (231.298) |
| 25 | 72.0 | Mean (SD) | 0.50 (0.50-1.00) | 155.19 (70.455) | 1338.10 (873.815) | 1343.30 (877.378) |
| 75 | 62.9 | Mean (SD) | 1.00 (0.50-1.50) | 334.00 (108.578) | 3038.41 (905.923) | 3050.34 (926.792) |
| 150 | 66.3 | Mean (SD) | 1.00 (0.50-6.00) | 585.00 (230.427) | 5037.31 (1425.590) | 5045.39 (1433.037) |
| 300 | 71.4 | Mean (SD) | 1.00 (0.50-3.00) | 828.00 (190.273) | 8178.17 (2390.301) | 8192.56 (2400.495) |

Comparing Table 5 and Table 6 with Table 7, the results indicate a substantially higher plasma level in human at the 25 and 75 mg doses in Cmax, and in AUC compared to dogs.

EXAMPLE 9

Preparation of the Hydrochloride, (1-Hydroxy-2-) Naphthoate and Benzolsulfonate Salt of the Invention The hydrochloride, (1-Hydroxy-2-) naphthoate and benzolsulfonate salt of the Invention may be prepared as described or similarly described below: 8 mg (6aR,9aS)-5, 6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in either 20:1 acetone:water, 90:10 methanol:water or isopropyl alcohol is reacted with 1 equivalent of the acid. Anti-solvent addition (diethyl ether as anti-solvent) is then used to help precipitation of solid materials. The salts may be isolated from the following system:

hydrochloride—(in Acetone/H₂O 20/1; isopropyl alcohol and MeOH/H₂O 90/10 after anti-solvent addition);

(1-hydroxy-2) Naphthoate—(in isopropyl alcohol and MeOH/H₂O 90/10 after anti-solvent addition);

benzosulfonate—(in Acetone/H₂O 20/1 after anti-solvent addition).

The invention claimed is:

1. The compound (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in an acid addition salt form selected from fumarate, hydrochloride, (1-hydrox-2)-naphthoate, benzosulfonate, phosphate, mesylate, tartrate, sulphate and hydrobromate.

2. The salt according to claim 1, wherein said salt is in crystallinic form.

3. The crystallinic salt form according to claim 2 selected from mesylate, fumarate, L-tartrate and phosphate salt crystals.

4. The salt crystals according to claim 3, wherein the salt crystals exhibit an X-ray powder diffraction pattern comprising at least five peaks having 2-theta angle values selected from the group consisting of 11.5, 12.1, 16.5, 16.9, 18.2, 18.9, 19.2, 19.6, 20.6, 21.3, 21.6, 22.9, 23.6, 24.4, 25.7, 27.7, 28.2 and 31.3 degrees, wherein the XRPD pattern is measured in a diffractometer using copper anode, at wavelength alpha1 of 1.5406 Å and wavelength alpha2 of 1.5444 Å; or at least five peaks having d-spacing values selected from the group consisting of 7.68, 7.28, 5.36, 5.23, 4.87, 4.71, 4.62, 4.52, 4.31, 4.17, 4.12, 3.88, 3.77, 3.65, 3.46, 3.22, 3.17 and 2.86 Å; and wherein the values have a ±10% deviation.

5. The salt crystals according to claim 3, wherein the salt crystals exhibit an X-ray powder diffraction pattern comprising at least five peaks having 2-theta angle values selected from 7.2, 8.0, 10.1, 11.2, 11.7, 12.5, 13.2, 14.4, 15.5, 16.0, 16.7, 17.3, 19.8, 20.3, 21.1, 21.9, 22.9, 23.6, 24.4, 24.9, 26.1, 26.6, 27.4, 27.9, 29.0, 29.8, 31.8, 32.6, 33.5, 35.1, 36.3, 38.3 and 39.0 degrees, wherein the XRPD pattern is measured in a diffractometer using copper anode, at wavelength alpha1 of 1.5406 Å and wavelength alpha2 of 1.5444 Å; or at least five peaks having d-spacing values selected from the group consisting of 12.27, 11.03, 8.74, 7.90, 7.53, 7.08, 6.69, 6.14, 5.71, 5.53, 5.31, 5.12, 4.49, 4.37, 4.21, 4.06, 3.88, 3.76, 3.45, 3.57, 3.41, 3.35, 3.26, 3.20, 3.07, 3.00, 2.82, 2.75, 2.67, 2.56, 2.47, 2.35 and 2.32 Å; and wherein the values have a ±10% deviation.

6. The salt crystals according to claim 3, wherein the salt crystals are phosphate salt crystals.

7. The salt crystals according to claim 6, wherein the salt crystals are mono-phosphate salt crystals.

8. The salt crystals according to claim 6, wherein the salt crystals are in mono-phosphate, non-solvate, non-hydrate salt form.

9. The salt crystals according to claim 6, wherein the salt crystals exhibit an X-ray powder diffraction pattern comprising one or more peaks having 2-theta angle values selected from the group consisting of 13.8, 16.3, 19.2, 23.2, 23.8 and 25.9 degrees, wherein the XRPD pattern is measured in a diffractometer using copper anode, at wavelength alpha of 1.5406 Å and wavelength alpha2 of 1.5444 Å; or one or more peaks having d-spacing values selected from the group consisting of 6.44, 5.45, 4.62, 3.83, 3.73 and 3.44 Å, and wherein the values have a ±10% deviation.

10. The salt crystals according to claim 6, wherein the salt crystals exhibit an X-ray powder diffraction pattern comprising at least five peaks having 2-theta angle values selected from the group consisting of 9.5, 13.8, 14.0, 16.3, 17.7, 18.5, 18.9, 19.2, 22.2, 22.8, 23.2, 23.8, 24.4, 25.9, 29.7, 31.4 and 32.9 degrees, wherein the XRPD pattern is measured in a diffractometer using copper anode, at wavelength alpha of 1.5406 Å and wavelength alpha2 of 1.5444 Å; or at least five peaks having d-spacing values selected from the group consisting of 15.36, 9.33, 6.44, 6.33, 5.45, 5.01, 4.80, 4.70, 4.62, 4.00, 3.89, 3.83, 3.73, 3.65, 3.44, 3.01, 2.85 and 2.73 Å; and wherein the values have a ±10% deviation.

11. The salt crystals according to claim 6, wherein the salt crystals exhibit an X-ray powder diffraction pattern comprising at least five peaks having 2-theta angle values selected from those set forth in Table 3 below:

TABLE 3

| No. | Pos. [°2Th.] | d-spacing [Å] | Height [cts] | Rel. Int. [%] |
|---|---|---|---|---|
| 1 | 5.7553 | 15.35618 | 1887.34 | 73.85 |
| 2 | 6.8867 | 12.8358 | 176.68 | 10.75 |
| 3 | 7.5188 | 11.75808 | 53.19 | 2.78 |
| 4 | 9.4821 | 9.32747 | 328.23 | 22.83 |
| 5 | 10.9511 | 8.07934 | 133.75 | 4.65 |
| 6 | 11.7509 | 7.53118 | 226.95 | 7.89 |
| 7 | 11.8625 | 7.46054 | 201.05 | 5.24 |
| 8 | 12.7859 | 6.92377 | 149.08 | 6.48 |
| 9 | 13.7504 | 6.44022 | 456.19 | 15.87 |
| 10 | 13.9906 | 6.33014 | 633 | 44.04 |
| 11 | 15.3855 | 5.75923 | 245.11 | 12.79 |
| 12 | 16.2789 | 5.44515 | 1277.75 | 100 |
| 13 | 17.2688 | 5.13515 | 241.96 | 10.52 |
| 14 | 17.6964 | 5.01205 | 312.05 | 18.99 |
| 15 | 18.5004 | 4.796 | 690.64 | 36.03 |
| 16 | 18.8841 | 4.6994 | 800.41 | 27.84 |
| 17 | 19.2158 | 4.61904 | 859.15 | 74.71 |
| 18 | 20.6821 | 4.29474 | 559.5 | 14.6 |
| 19 | 22.2013 | 4.00417 | 641.59 | 50.21 |
| 20 | 22.8385 | 3.89388 | 682.56 | 41.55 |
| 21 | 23.2185 | 3.83102 | 555.61 | 24.16 |
| 22 | 23.8425 | 3.73215 | 697.52 | 54.59 |
| 23 | 24.4086 | 3.64685 | 357.59 | 18.66 |
| 24 | 25.8905 | 3.44137 | 842.43 | 29.3 |
| 25 | 27.9329 | 3.19423 | 221.79 | 11.57 |
| 26 | 29.6611 | 3.01192 | 250.43 | 26.13 |
| 27 | 31.3753 | 2.85118 | 306.23 | 15.98 |
| 28 | 32.863 | 2.72542 | 167.88 | 20.44 |
| 29 | 34.6203 | 2.591 | 111.05 | 7.73 |
| 30 | 36.2262 | 2.47975 | 92.41 | 4.82 |
| 31 | 37.5261 | 2.39678 | 105.94 | 6.45 |

TABLE 3-continued

| No. | Pos. [°2Th.] | d-spacing [Å] | Height [cts] | Rel. Int. [%] |
|---|---|---|---|---|
| 32 | 41.1361 | 2.19441 | 25.77 | 4.03 |
| 33 | 45.786 | 1.98015 | 21.45 | 4.92 | wherein the XRPD pattern is measured in a diffractometer using copper anode, at wavelength alpha1 of 1.5406 Å and wavelength alpha2 of 1.5444 Å; and wherein the 2-theta values have a ±10% deviation.

12. The salt crystals of claim 11 which exhibit an X-ray powder diffraction pattern comprising at least four peaks having d-spacing values selected from those set forth in claim 11, wherein the D-spacing values have a ±10% deviation.

13. The salt crystals which exhibit an X-ray powder diffraction pattern corresponding with or substantially as herein set forth in claim 11.

14. The salt crystals according to claim 6, wherein said salt crystals exhibit an X-ray powder diffraction pattern corresponding with or substantially as herein depicted in FIG. 3-A.

15. The salt crystals according to claim 6, wherein the salt crystals exhibit a Thermal Gravimetric Analysis (TGA) pattern comprising a peak with a melting temperature of about 202°-212° C., e.g., about 207° C.-208° C.; or exhibit a Thermal Gravimetric Analysis (TGA) pattern corresponding with or substantially as herein depicted in FIG. 3-B.

16. The salt crystals according to claim 6, wherein the salt crystals exhibit a Differential Scanning Calorimetry (DSC) pattern comprising a peak with an endotherm at about 213° C.; or exhibit a Differential Scanning Calorimetry (DSC) pattern corresponding with or substantially as herein depicted in FIG. 3-C.

17. The salt crystals according to claim 3, wherein said salt crystals are mesylate salt crystals.

18. The salt crystals according to claim 17, wherein the salt crystals exhibit an X-ray powder diffraction pattern corresponding with or substantially as depicted in FIG. 1-A.

19. The salt crystals according to claim 3, wherein said salt crystal is a fumarate salt crystal.

20. The salt crystals according to claim 19, wherein said salt crystals exhibit an X-ray powder diffraction pattern corresponding with or substantially as depicted in FIG. 2-A.

21. The salt crystals according to claim 3, wherein said salt crystal is an L-tartrate salt crystal.

22. The salt crystals according to claim 21, wherein said salt crystals exhibit an X-ray powder diffraction pattern corresponding with or substantially as depicted in FIG. 4-A.

23. The compound according to claim 1, wherein the acid addition salt is selected from fumarate, hydrochloride, (1-hydrox-2)-naphthoate, benzosulfonate, phosphate, mesylate, tartrate, sulphate and hydrobromate salt.

24. A pharmaceutical composition comprising the compound according to claim 1, as active ingredient, together with a pharmaceutically acceptable diluent or carrier.

25. A pharmaceutical composition comprising the salt crystals according to claim 2, as active ingredient, together with a pharmaceutically acceptable diluent or carrier.

26. A pharmaceutical composition comprising the salt crystals according to claim 9, as active ingredient, together with a pharmaceutically acceptable diluent or carrier.

27. A process for the production of the salt crystals according to claim 6, comprising the steps of reacting (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one with phosphoric acid in a solvent.

28. The process according to claim 27, wherein the phosphoric acid is in the amount of about 1 molar equivalent of phosphoric acid to one molar equivalent of the free base.

29. The process according to claim 27, wherein the phosphoric acid is in the amount of about 0.5 molar equivalent of phosphoric acid to one molar equivalent of the free base.

30. The process according to claim 27, wherein the solvent is selected from acetonitrile and methanol.

31. The process according to claim 27, wherein the free base is dissolved in the solvent acetonitrile and the ratio of acetonitrile to free base is about 11 mL of acetonitrile to 1 mg of free base.

* * * * *